US006979448B1

(12) United States Patent
Bendig et al.

(10) Patent No.: US 6,979,448 B1
(45) Date of Patent: *Dec. 27, 2005

(54) CHIMAERIC PLANT VIRUSES WITH MUCIN PEPTIDES

(75) Inventors: Mary Bendig, Vesenaz (CH); Tim Jones, Babraham (GB); Koen Hellendoorn, Newmarket (GB)

(73) Assignee: The Dow Chemical Company, Midland, MI (US)

( * ) Notice: Subject to any disclaimer, the term of this patent is extended or adjusted under 35 U.S.C. 154(b) by 315 days.

This patent is subject to a terminal disclaimer.

(21) Appl. No.: 10/070,566

(22) PCT Filed: Sep. 11, 2000

(86) PCT No.: PCT/GB00/03500

§ 371 (c)(1),
(2), (4) Date: Mar. 7, 2002

(87) PCT Pub. No.: WO01/18199

PCT Pub. Date: Mar. 15, 2001

(30) Foreign Application Priority Data

Sep. 9, 1999 (GB) .................................. 9921337

(51) Int. Cl.[7] ........................ A61K 39/12; A61K 48/00
(52) U.S. Cl. ............... 424/199.1; 424/93.2; 424/204.1; 424/205.1
(58) Field of Search ...................... 435/320.1; 800/278; 424/186.1, 199.1, 204.1, 205.1, 93.2

(56) References Cited

U.S. PATENT DOCUMENTS

| 4,963,484 | A |   | 10/1990 | Kufe ........................ 435/69.3 |
| 5,053,489 | A |   | 10/1991 | Kufe ........................ 530/350 |
| 5,874,087 | A | * | 2/1999 | Lomonossoff et al. ... 424/199.1 |
| 5,958,422 | A | * | 9/1999 | Lomonossoff ........... 424/199.1 |
| 6,110,466 | A | * | 8/2000 | Lomonossoff et al. ... 424/199.1 |

FOREIGN PATENT DOCUMENTS

| WO | WO 92/18618 | 10/1992 | ............ C12N 7/01 |
| WO | WO 96/02649 | 2/1996 | .......... C12N 15/40 |
| WO | WO 98/37095 | 8/1998 | .......... C07K 14/00 |
| WO | WO 98/50527 | 11/1998 | ............ C12N 5/08 |
| WO | WO 98/56933 | 12/1998 | .......... C12N 15/82 |

OTHER PUBLICATIONS

Port et al., Virology, 1994, vol. 202, pp. 949-955.*
Almeida and Alpar, "Nasal delivery of vaccines," *J Drug Target*, 3:455-467, 1996.
Apostolopoulos and McKenzie, "Cellular mucins: targets for immunotherapy," *Crit Rev Immunol*, 14:293,309, 1994.
Burchell et al., "Complexity of expression of antigenic determinants, recognized by monoclonal antibodies HMFG-1 and HMFG-2, in normal and malignant human mammary epithelial cells," *J Immunol*, 131:508-513, 1983.

Dalsgaard et al., "Plant-derived vaccine protects target animals against a viral disease," *Nature Biotechnol*, 15:248-252, 1997.
Dessens and Lommonossoff, "Cauliflower mosaic virus 35S promoter-controlled DNA copies of cowpea mosaic virus RNAs are infectious on plants," *J Gen Virol*, 74:889-892, 1993.
Dolja and Koonin, "Phylogeny of capsid proteins of small icosahedral RNA plant viruses," *J Gen Virol*, 72:1481-1486, 1991.
Graham et al., "Intramuscular immunisation with MUC1 cDNA can protect C57 mice challenged with MUC1-expressing syngeneic mouse tumour cells," *Int J Cancer*, 65:664-670, 1996.
Kaminksi et al., "Importance of antibody isotype in monoclonal anti-idiotype therapy of a murine B cell lymphoma. A study of hybridoma class switch variants," *J Immunol*, 136:1123-1130, 1986.
Modelska et al., "Immunization against rabies with plant-derived antigen," *Proc Natl Acad Sci, USA*, 95:2481-2485, 1998.
Mosmann et al., "Two types of murine helper T cell clone. I. Definition according to profiles of lymphokine activities and secreted proteins," *J Immunol*, 136:2348-2357, 1986.
Porta et al., "Development of cowpea mosaic virus as a high-yielding system for the presentation of foreign peptides," *Virology*, 202:949-955, 1994.
Usha et al., "Expression of an animal virus antigenic site on the surface of a plant virus particle," *Virology*, 197:366-374, 1993.
Zhang et al., "Augmenting the immunogenicity of synthetic MUC1 peptide vaccines in mice," *Cancer Research*, 56:3315-3319, 1996.
Akagi et al., "Therapeutic antitumor response after immunization with an admixture of recombinant vaccinia viruses expressing a modified MUC1 gene and the murine T-cell costimulatory molecule B7," *J Immunother*, 20:38-47, 1997.
Balloul et al., "Recombinant MUC1 vaccinia virus: a potential vector for immunotherapy of breast cancer," *Cell Mol Biol* (Noisy-le grand), 40(SI):49-59, 1994.
Graham et al., "The polymorphic epithelial mucin: potential as an immunogen for a cancer vaccine," *Cancer Immunol Immunother*, 42:71-80, 1996.
Liu et al., "Structurally defined synthetic cancer vaccines: analysis of structure, glycosylation and recognition of cancer associated mucin, MUC-1 derived peptides," *Glycoconj J*, 12:607-617, 1995.

* cited by examiner

*Primary Examiner*—Ashwin Mehta
(74) *Attorney, Agent, or Firm*—Medlen & Carroll LLP

(57) ABSTRACT

Mucin peptide epitopes are inserted into the coat protein of a plant virus (e.g., a comovirus such as CPMV) having a beta-barrel structure at an immunogenically effective site, such as in a loop connecting beta sheets or at/near the C-terminus. The resulting chimaeric virus particles are extremely immunogenic, giving better results than KLH conjugation and not requiring the addition of exogenous adjuvant. They are effective at mucosal surfaces, particularly when administered intranasally.

18 Claims, 26 Drawing Sheets

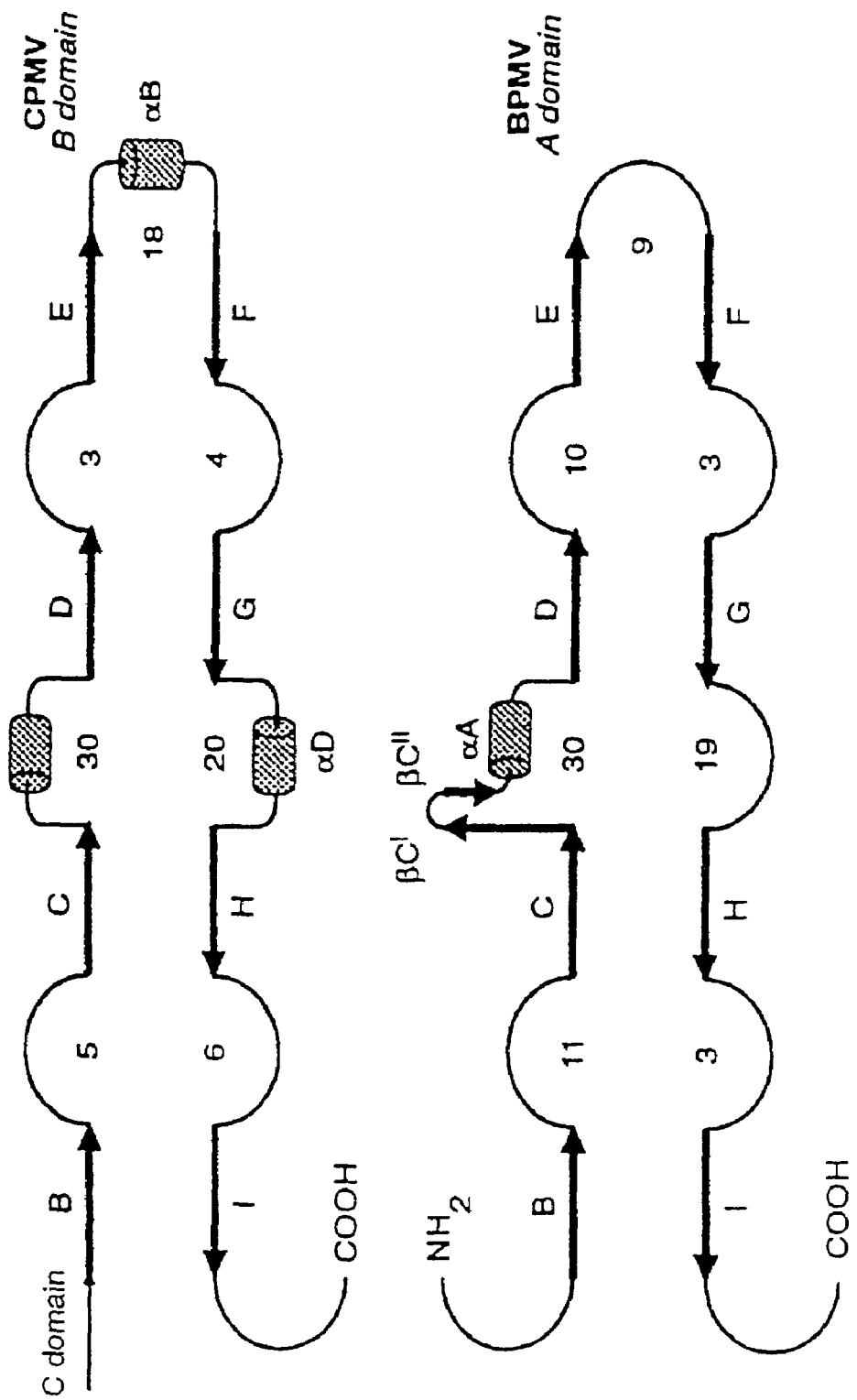

FIG. 1(contd.)

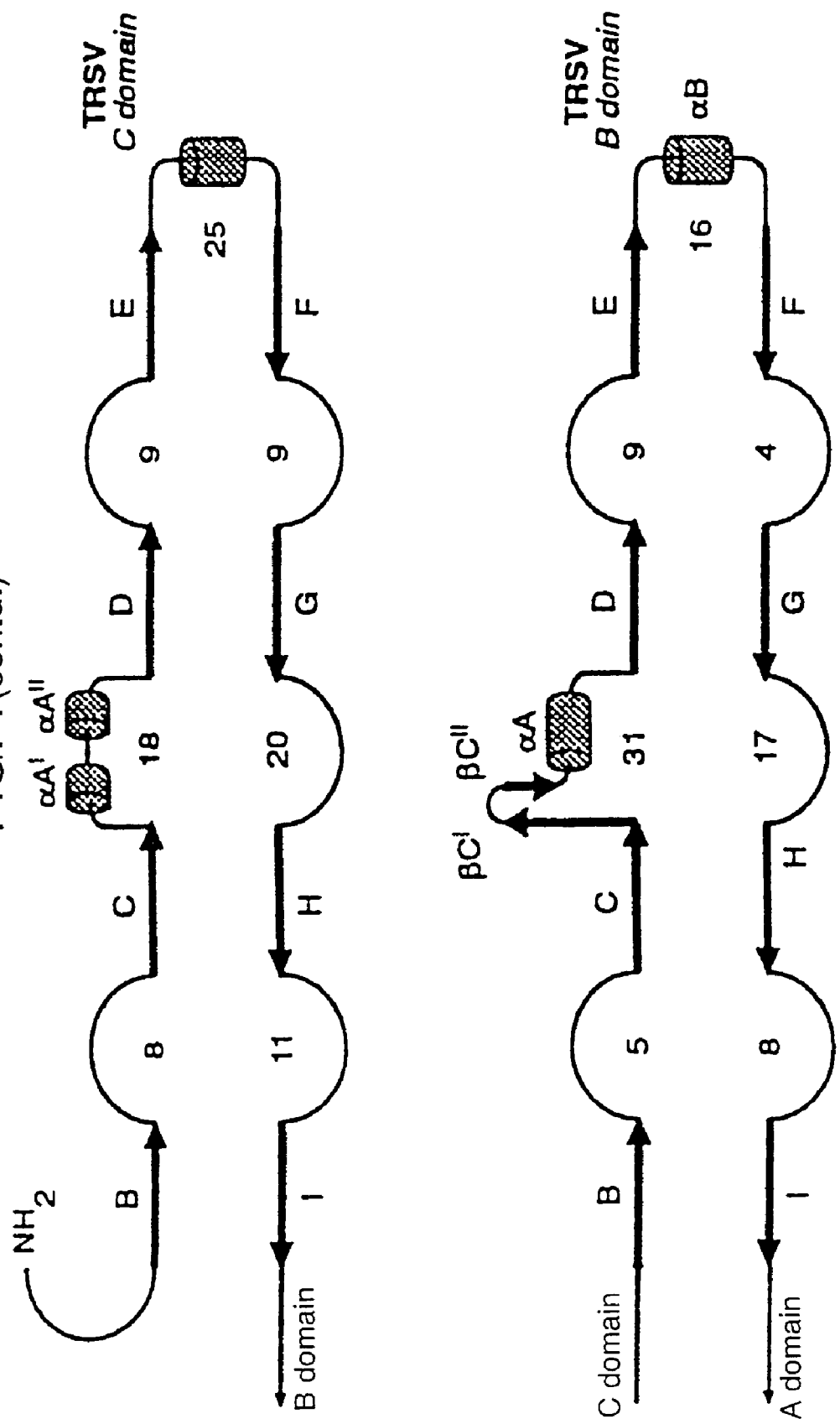
FIG. 1(contd.)

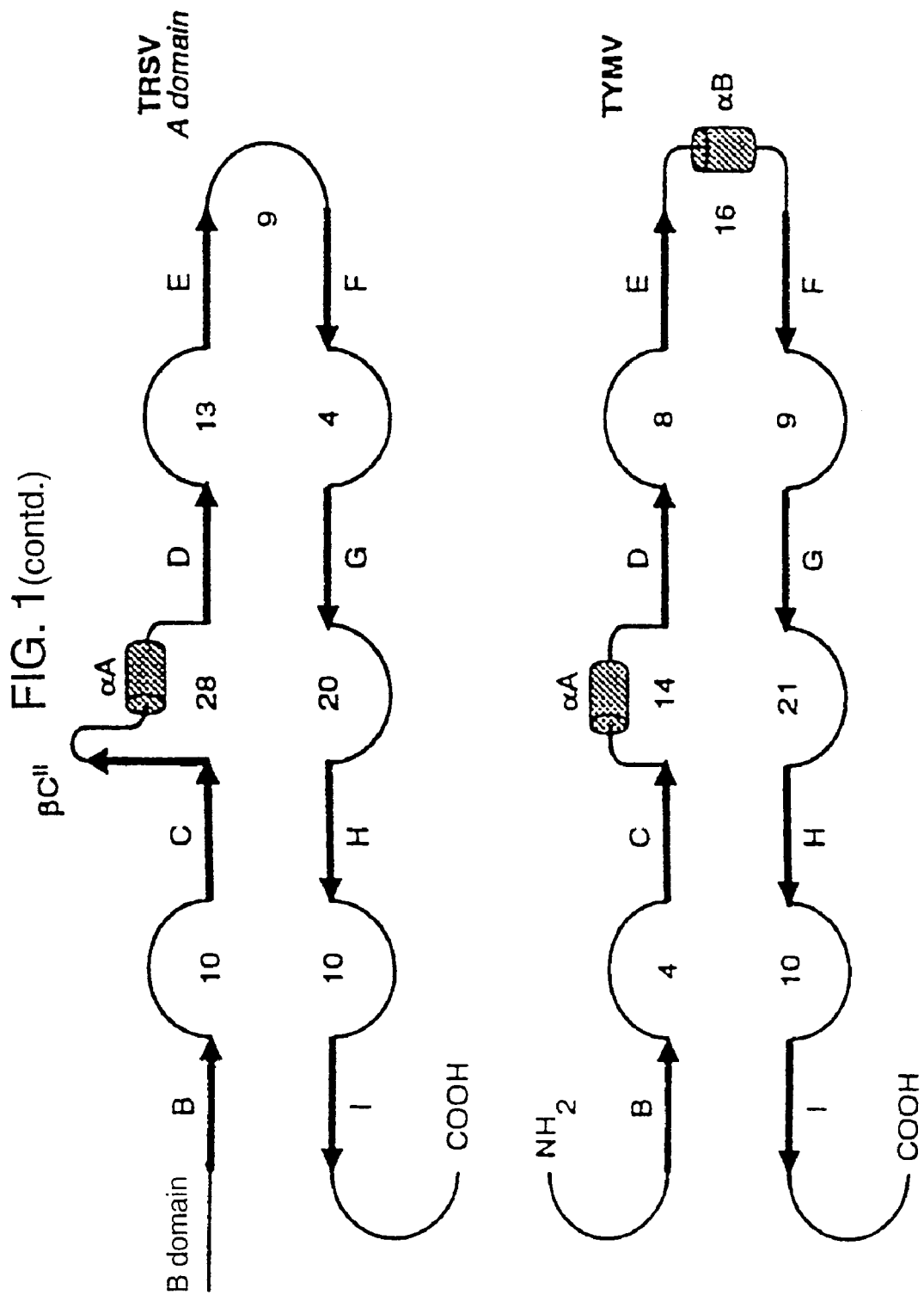
FIG. 1(contd.)

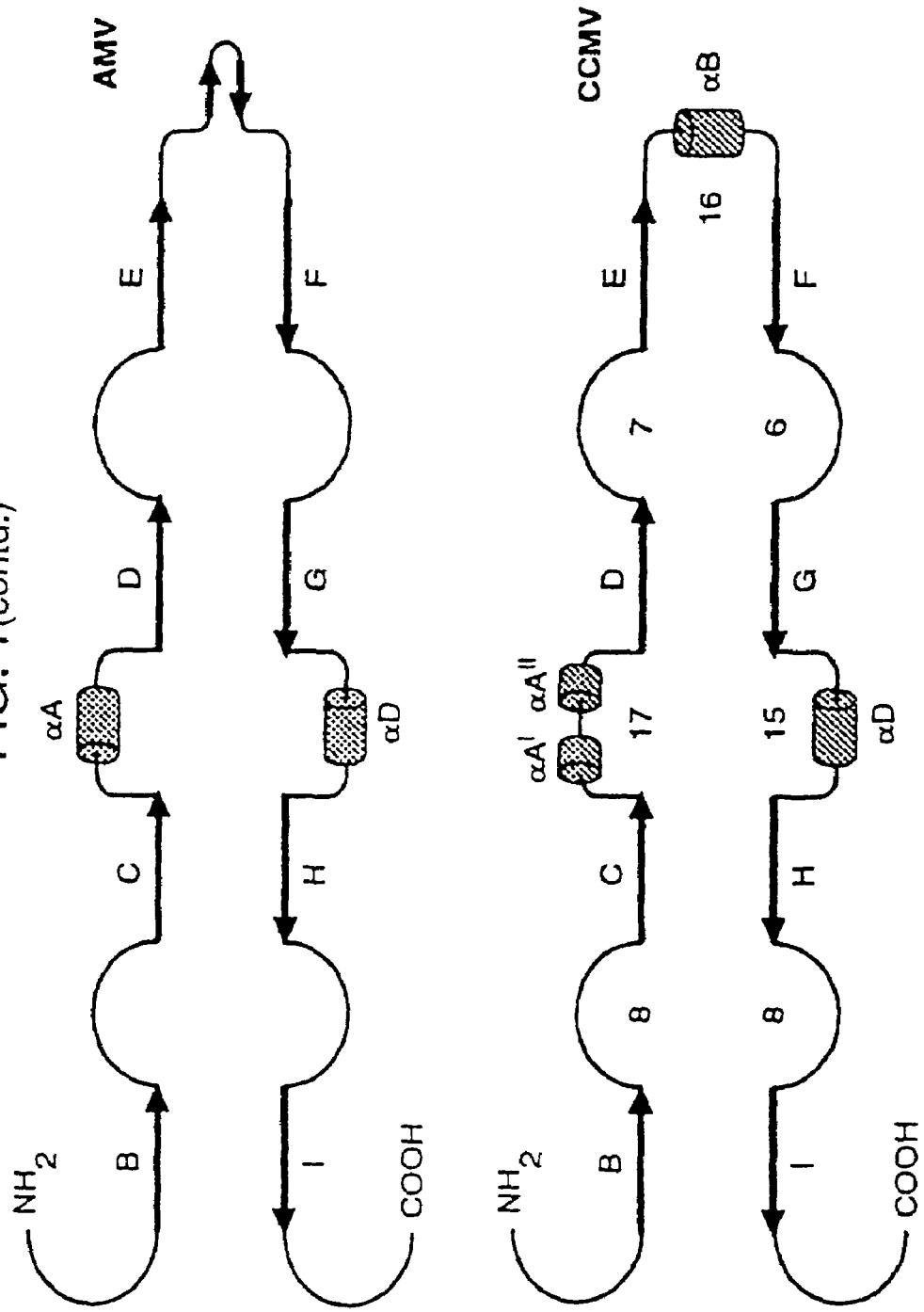
FIG. 1 (contd.)

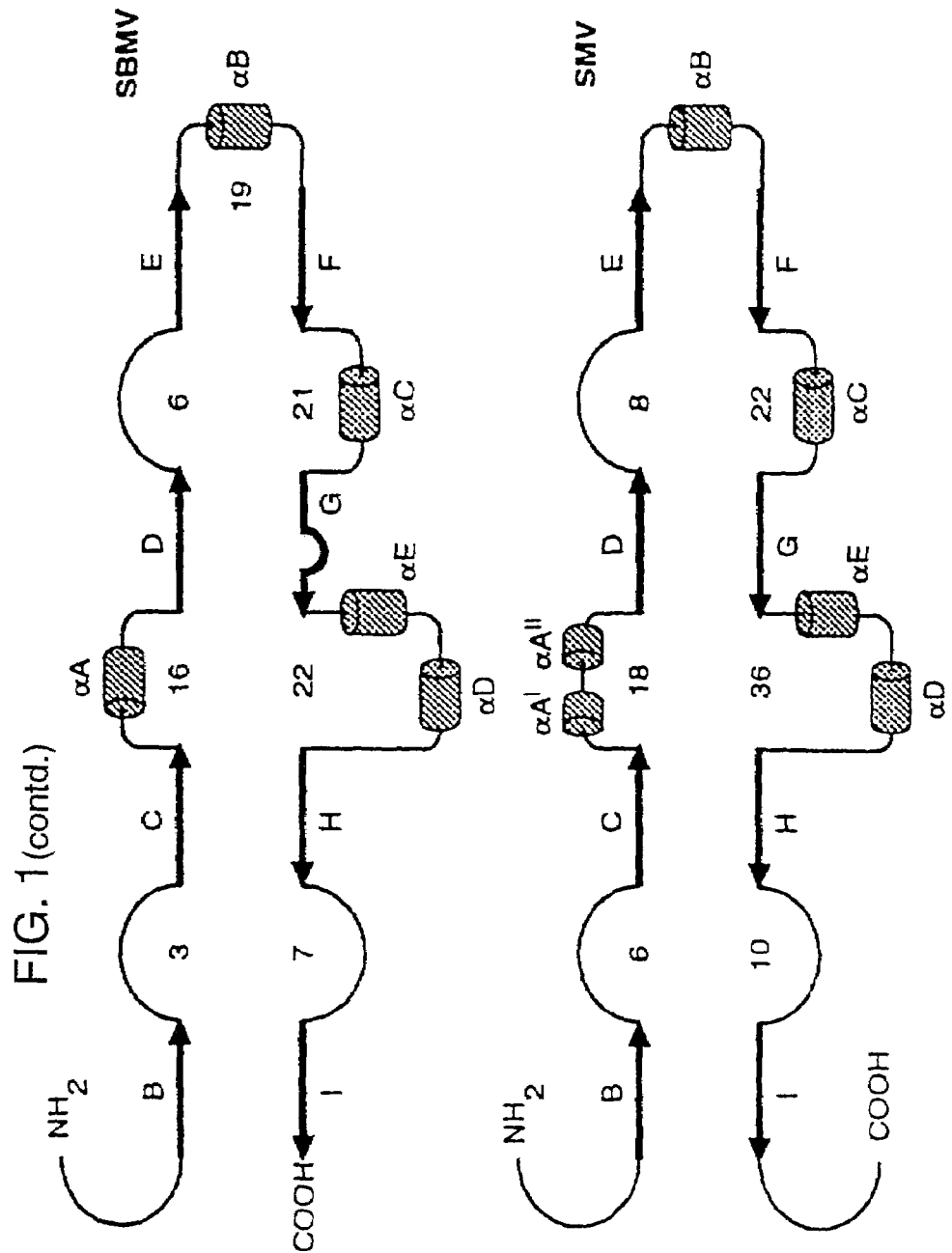
FIG. 1(contd.)

FIG. 1(contd.)

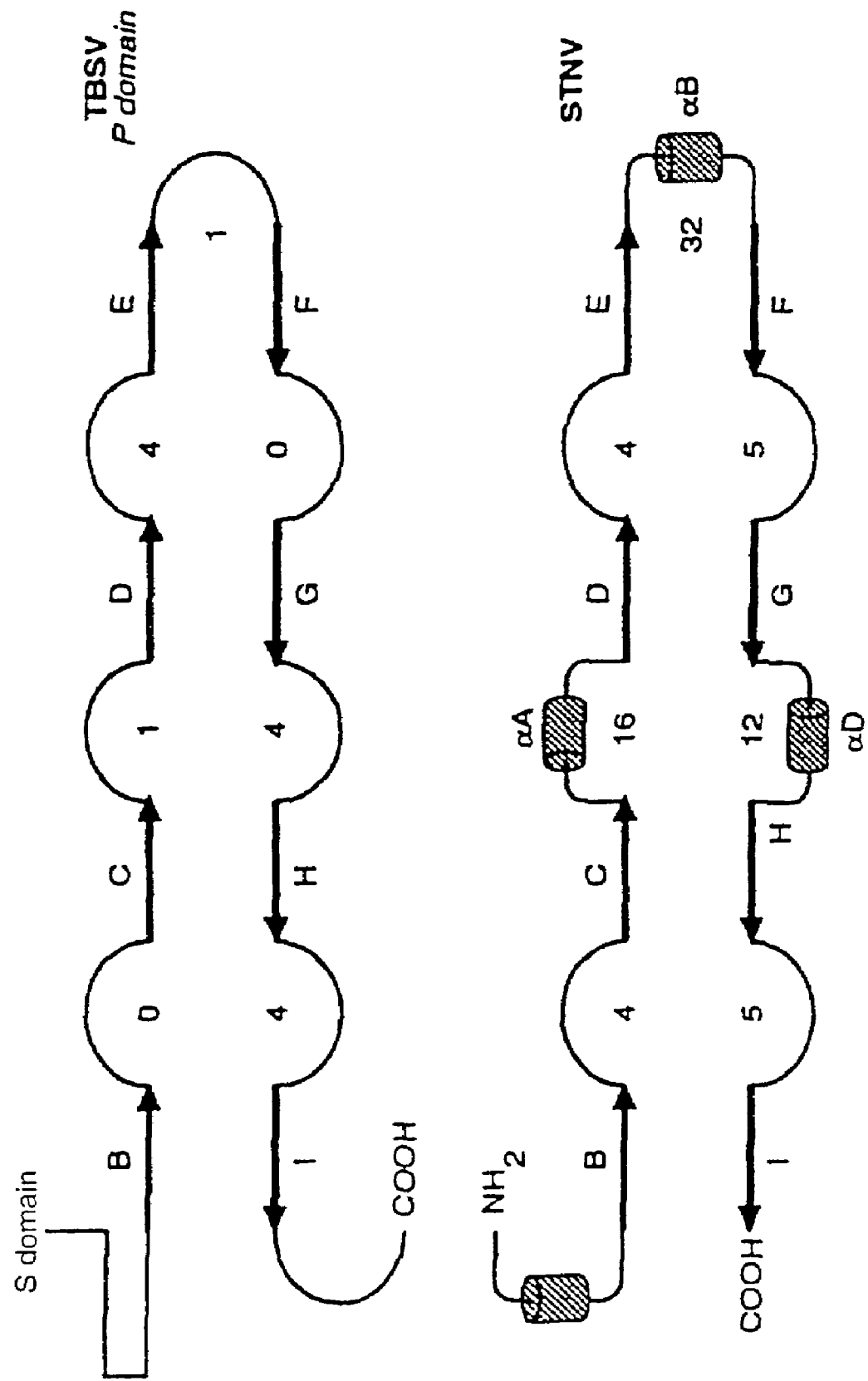
FIG. 1(contd.)

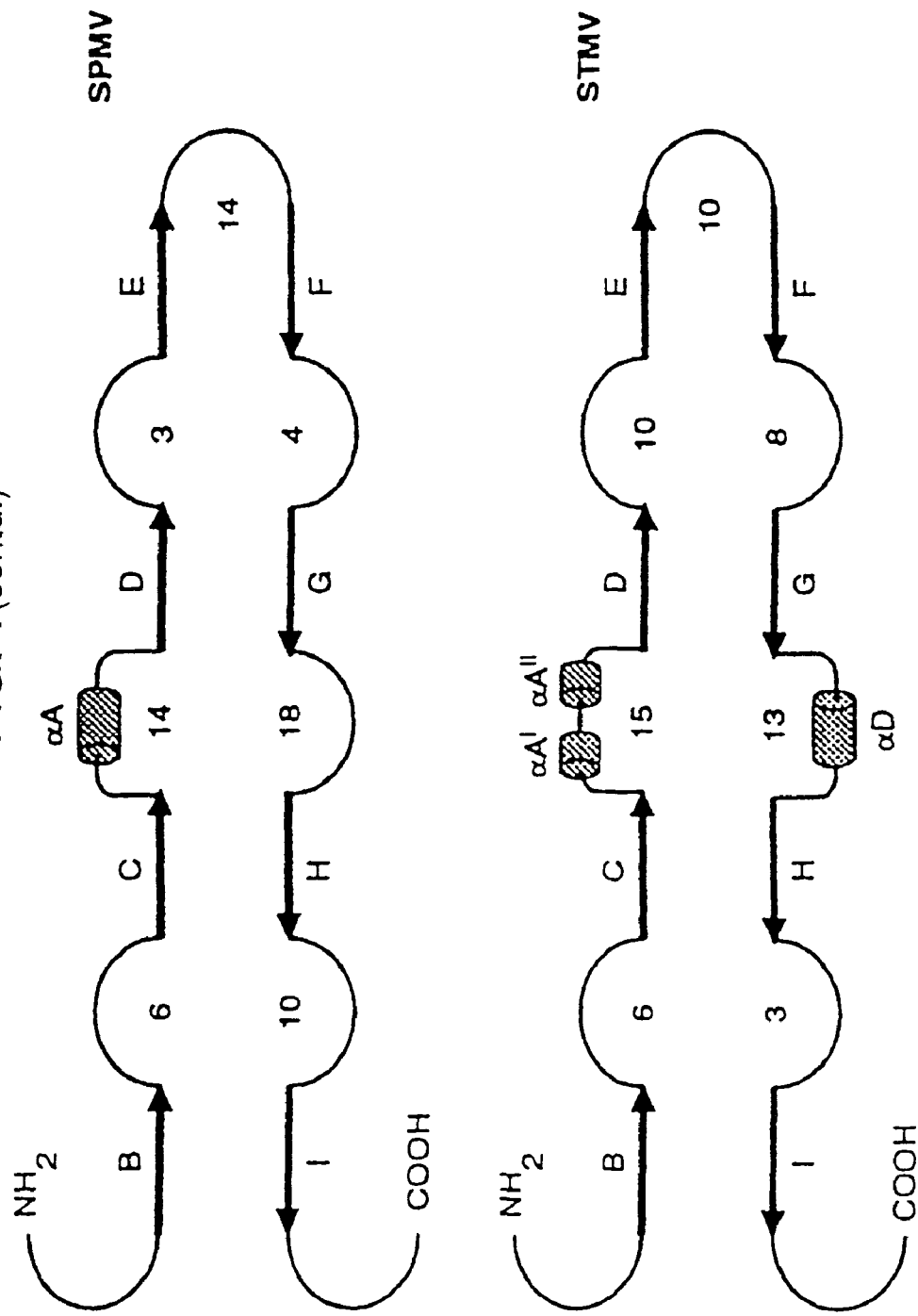
FIG. 1 (contd.)

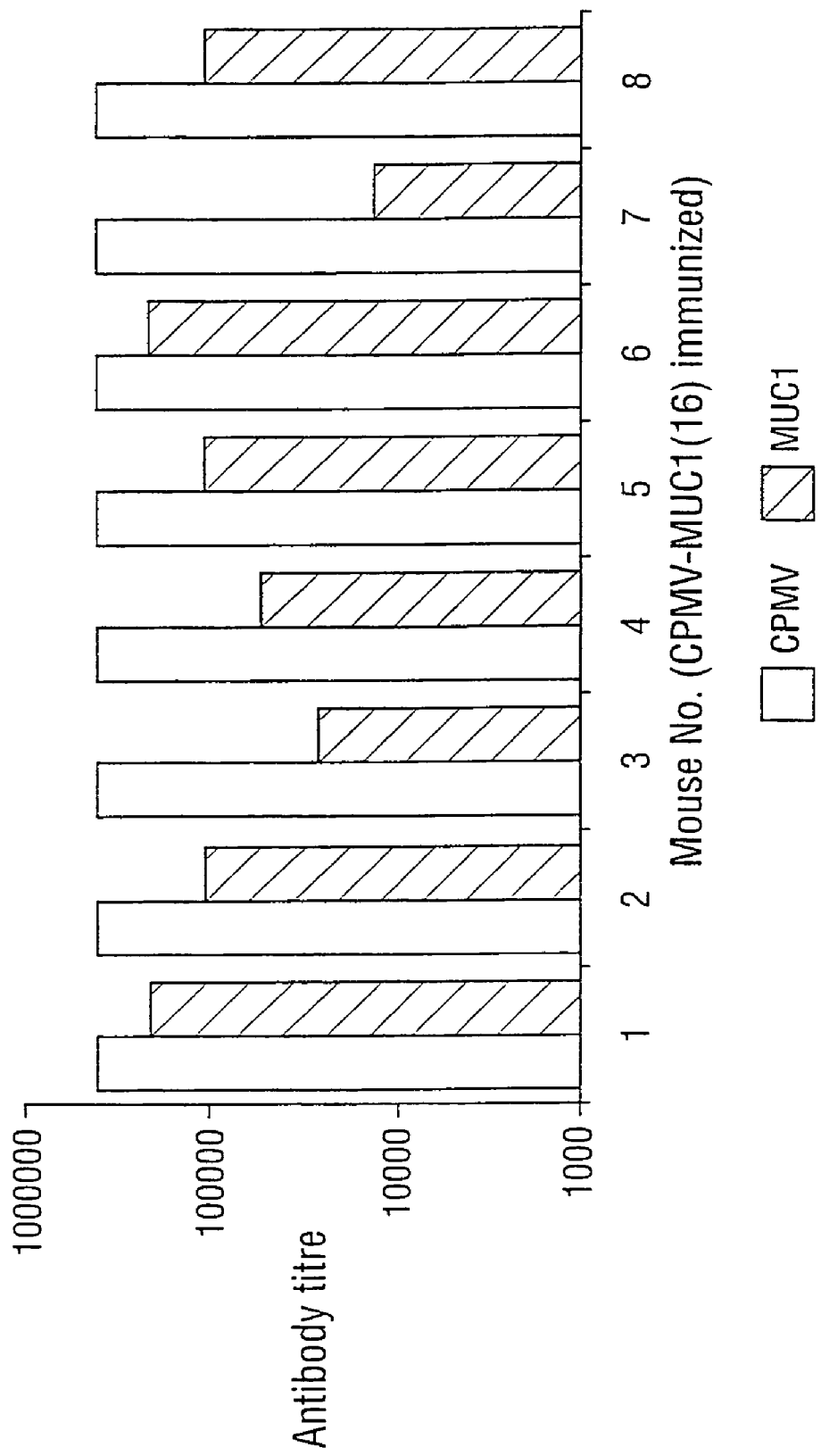

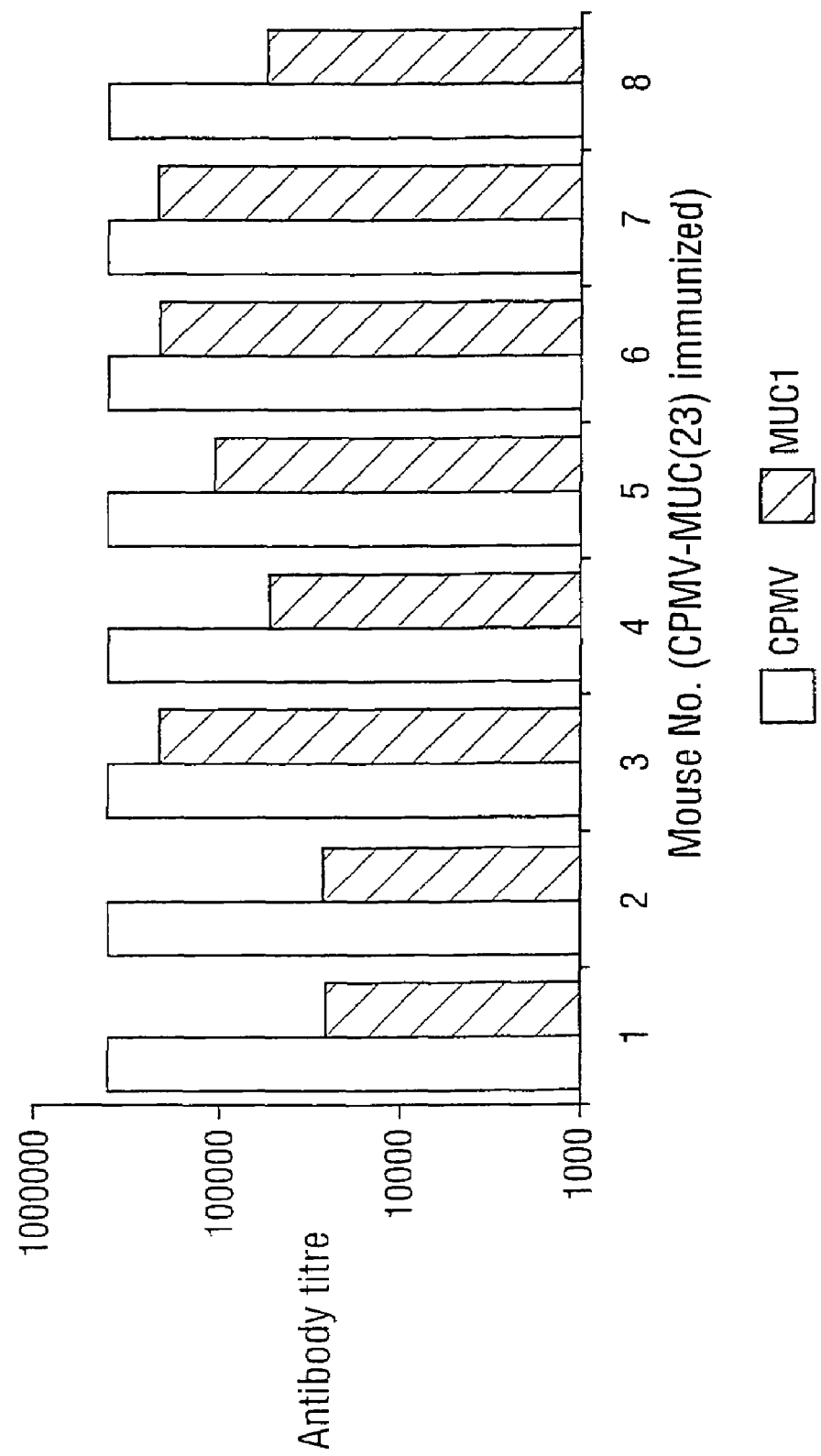

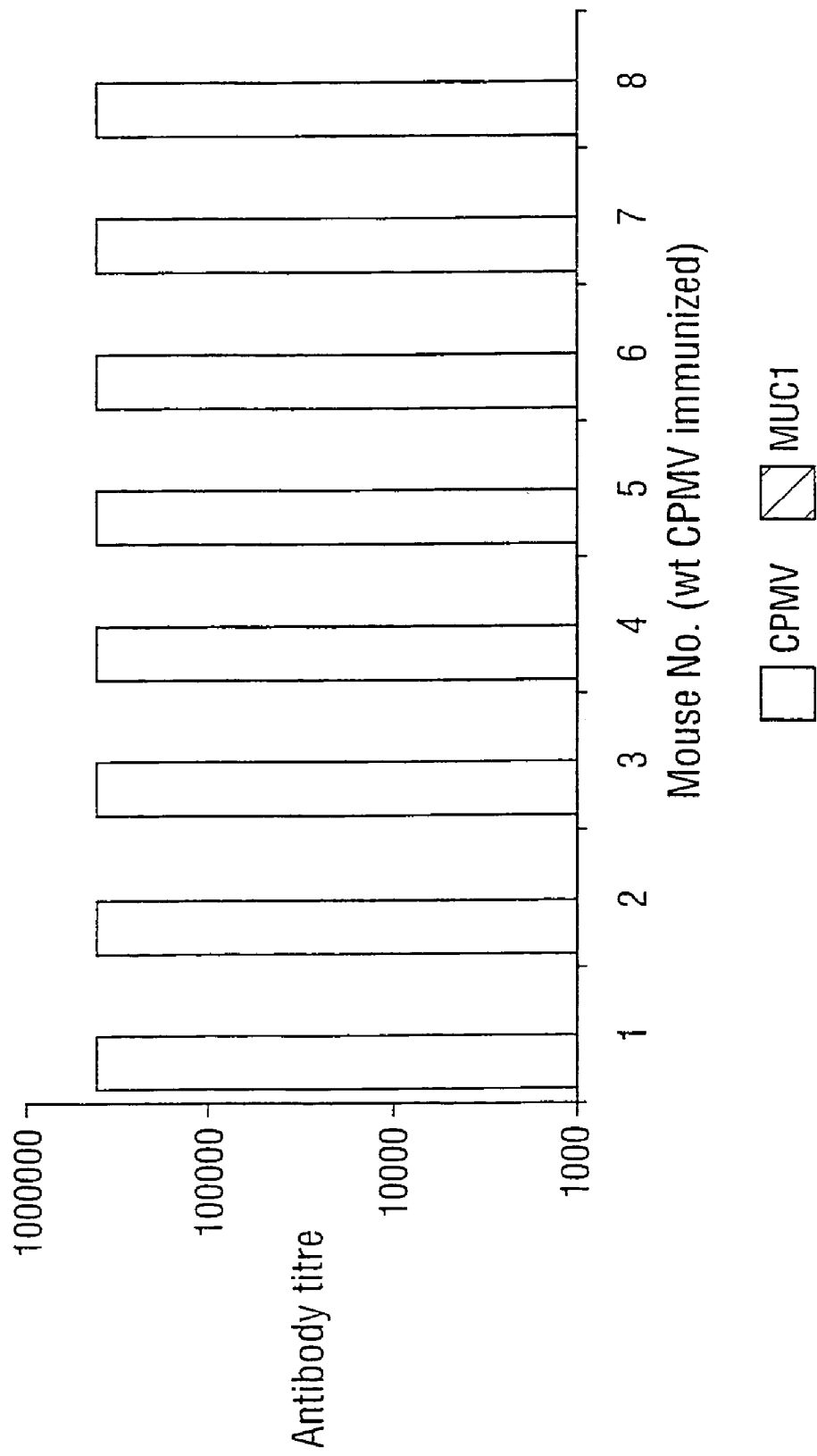

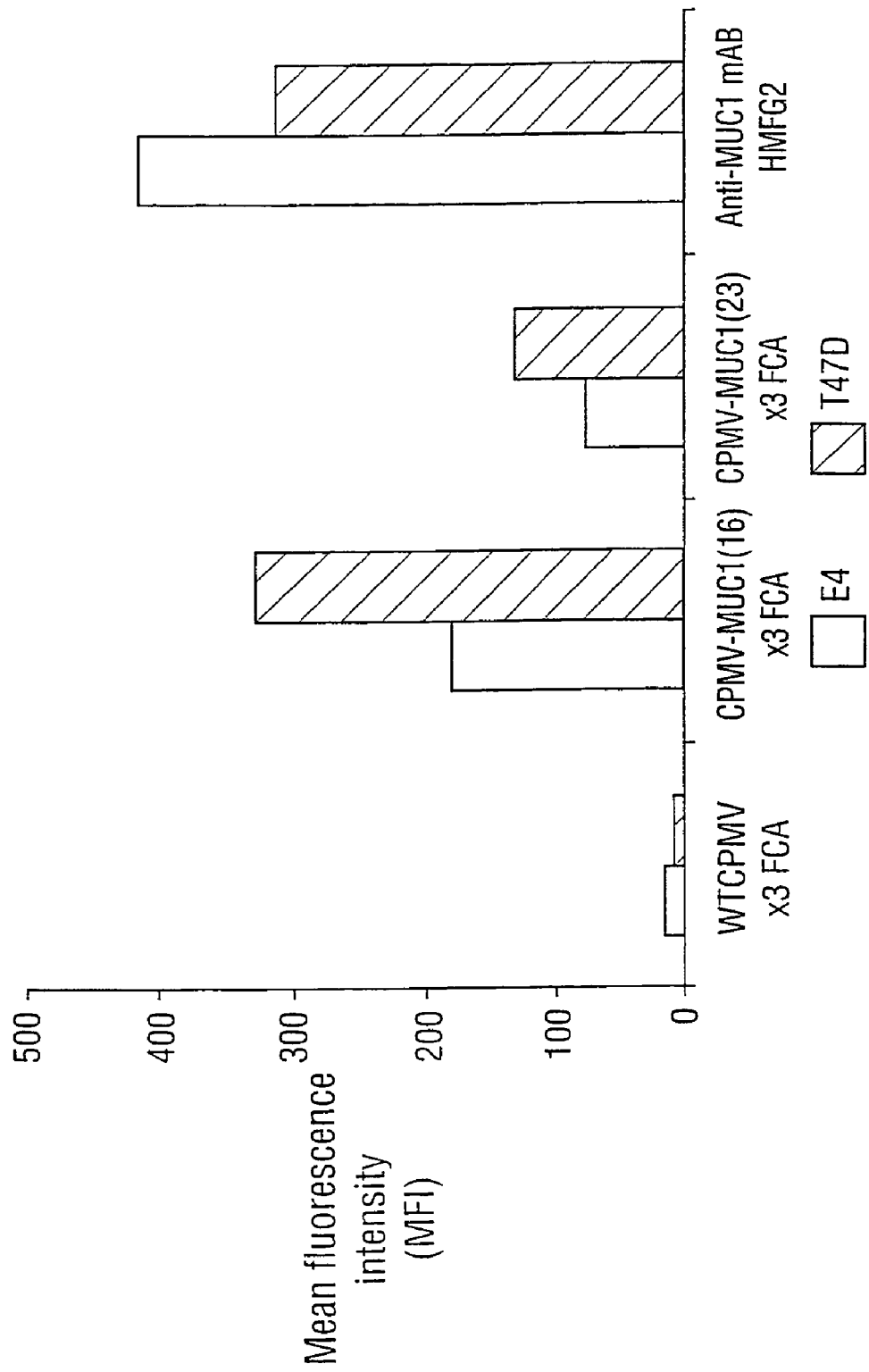

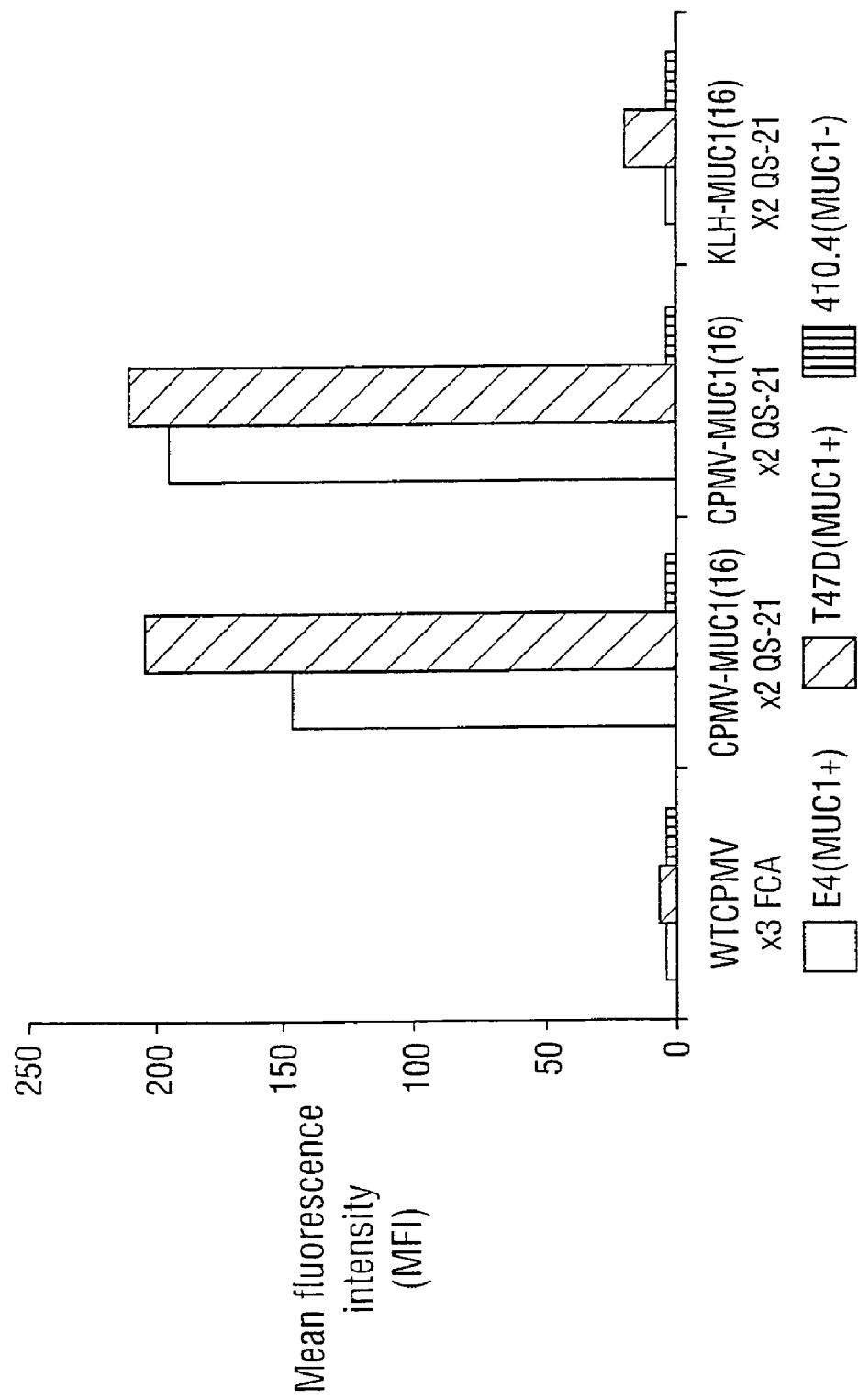

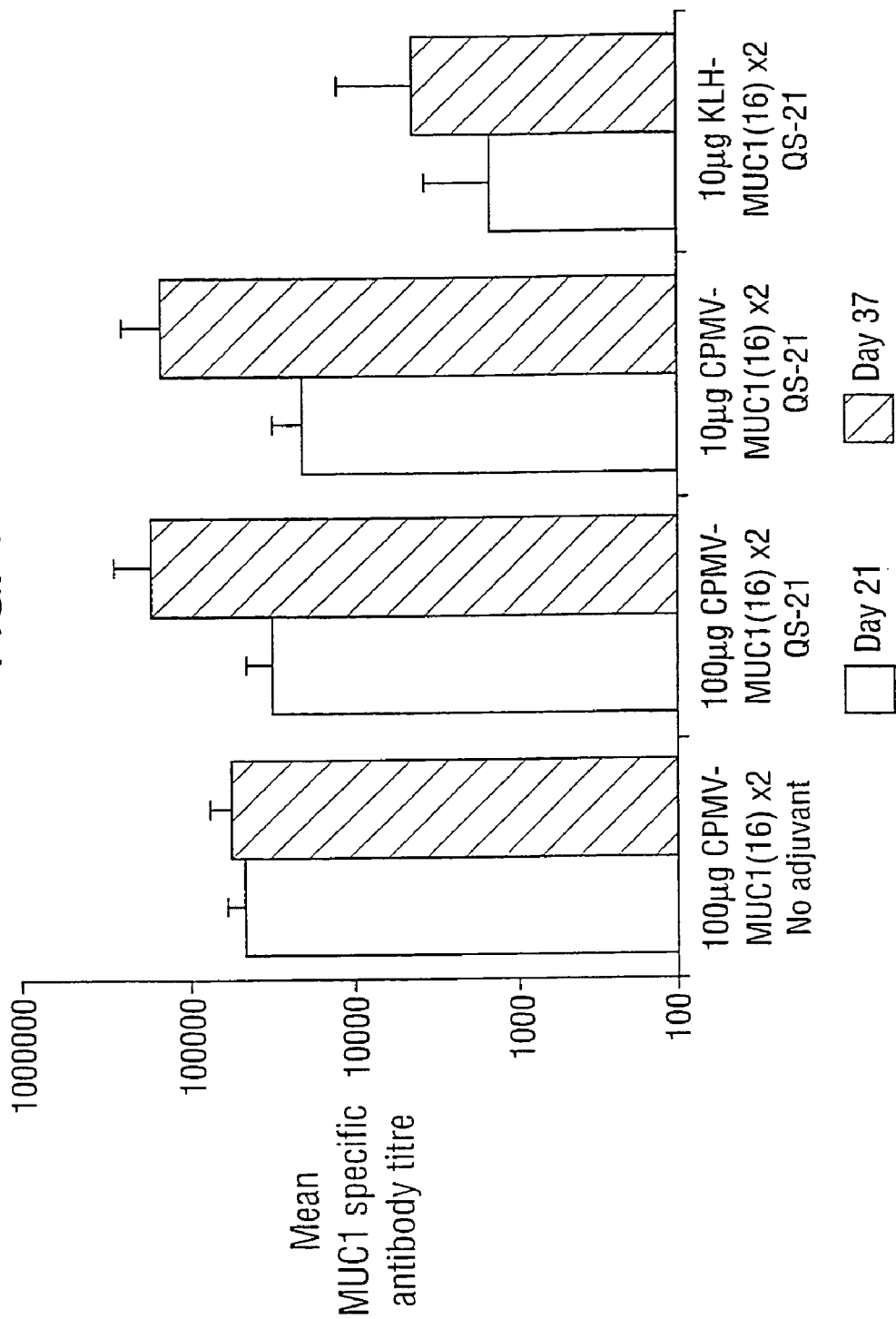

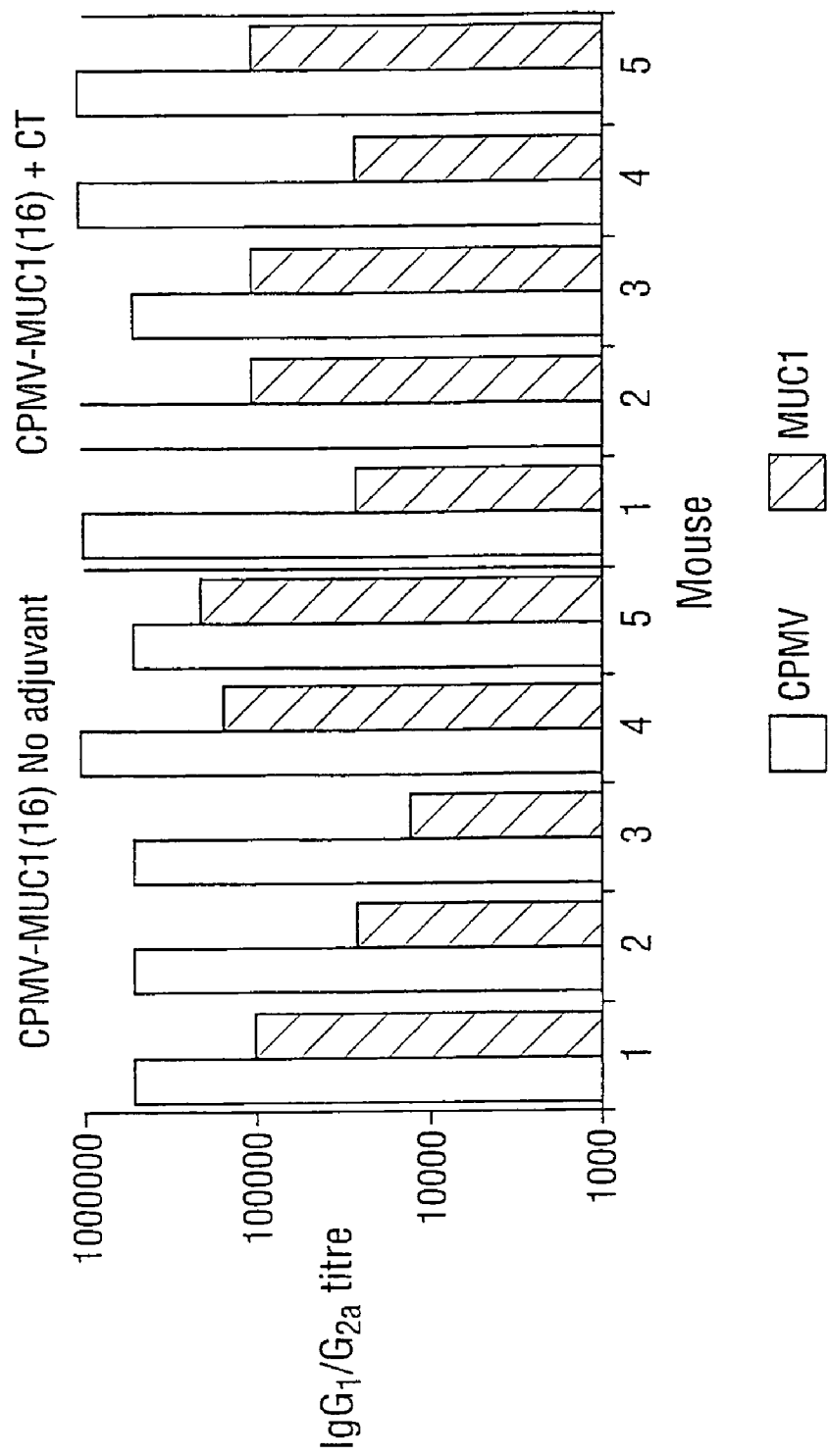

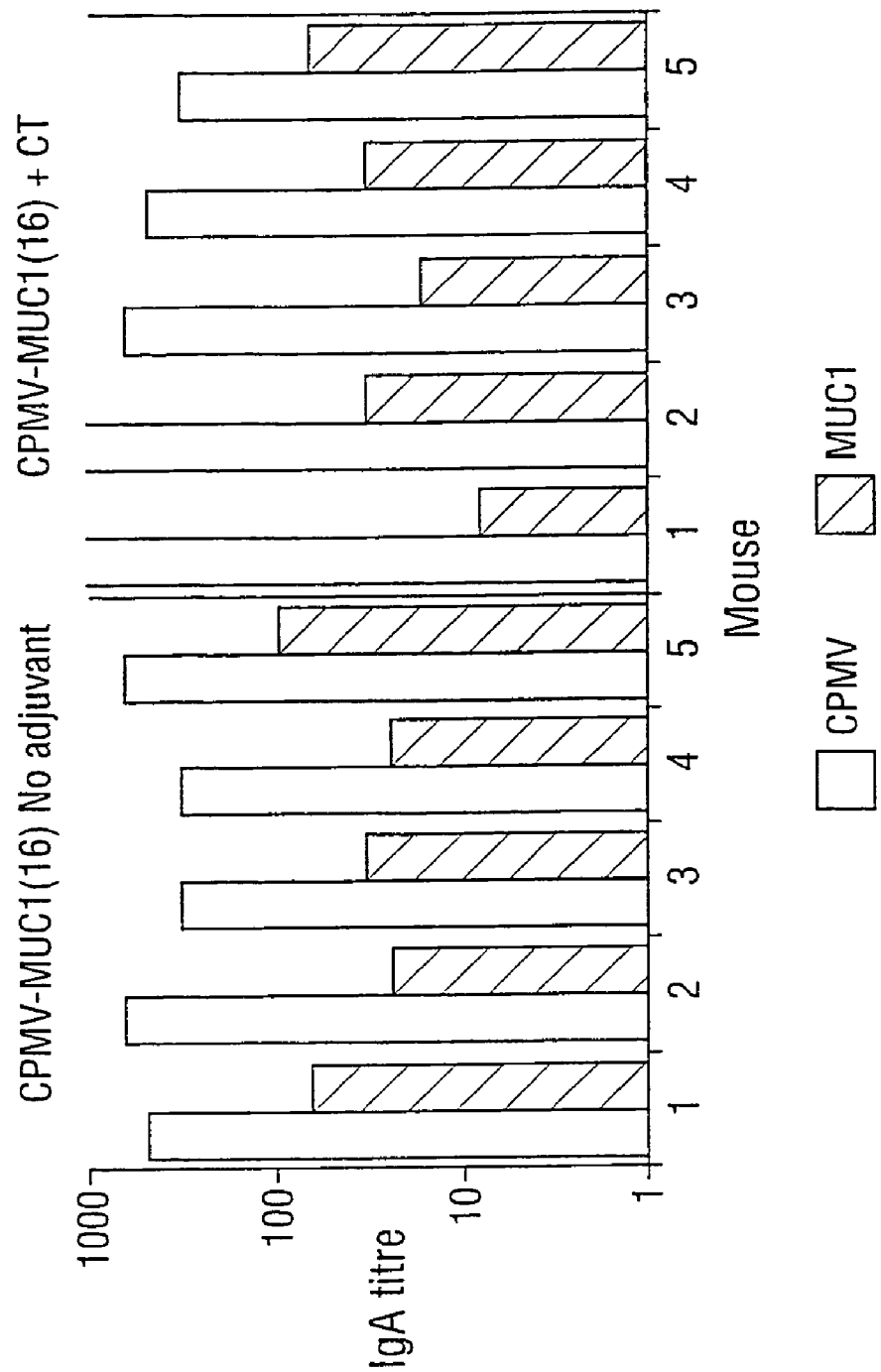

FIG. 8(a)

Sequence of SBMV Coat Protein Spanning The Potential Insertion Site With Introduced Base Changes and New Restriction Sites: (sequence starts at nt 3955)

```
    M   E   G   G   S   S   K   T   A   V   N   T   G
    ATGGAAGGAGGATCATCTAAGACTGCTGTGAACACTGGG
              ↓                       ↓
            GGATCC                  GTTAAC
            BamH I                   Hpa I
```

FIG. 8(b)

Series of Sequences to be Inserted Between the Restriction Sites to Insert the MUC1(16) Epitope at Various Locations

```
     G   V   T   S   A   P   D   T   R   P   A   P   G   S   T   A
     GGTGTTACTTCTGCTCCTGATACTAGACCTGCTCCTGGTTCTACTGCT
     CCACAATGAAGACGACCACTATGATCTGGACGAGGACCAAGATGACGA
    ←                          ↓   ↓                           →
```

| | |
|---|---|
| GATCC | TCTAAGACTGCTGTT |
| G | AGATTCTGACGACAA |
| | |
| GATCCTCT | AAGACTGCTGTT |
| GAGA | TTCTGACGACAA |
| | |
| GATCCTCTAAG | ACTGCTGTT |
| GAGATTC | TGACGACAA |
| | |
| GATCCTCTAAGACT | GCTGTT |
| GAGATTCTGA | CGACAA |
| | |
| GATCCTCTAAGACTGCT | GTT |
| GAGATTCTGACGA | CAA |

FIG. 9

```
LTSV : NI---YAPARLTIAA-ANSSINIASVGTLYATYEVEL
SBMV : NIGNILVPARLVIAMEGGSSKTAVNTGRLYASYTIRL
SMV  : NIATDLVPARLVIALLDGSSSTAVAAGRIYASYTIQM
       ######=======##############
        βH      loop        βI
```

FIG. 13

```
                    220       230       240
         AA        |ASIVQKYVIDLGGTLTSFEGPSYLMPP
         PHD sec   | HHHHHEEEE    EEEE    EEEEE
         Rel sec  |14543224452551562558648762 4
detail :
         prH sec   |46665532111110000000000000 0
         prE sec   |10112345663224675221268875 3
         prL sec   |42222111224664223778731124 6
subset : SUB sec   |..H......E.LL.EE.LLLL.EEE..
```

Abbreviations :
 AA : amino acid sequence
 H : helix
 E : extended (sheet)
 blank : other (loop)
 PHD : Profile network prediction HeiDelberg
 Rel : Reliability index of prediction (0-9)
 prH : probability for assigning helix
 prE : probability for assigning strand
 prL : probability for assigning loop
 SUB : a subset of the prediction, for all residues with an average expected accuracy of >82%

FIG. 10(a)

Sequence of LTSV Coat Protein Spanning The Potential Insertion Site With Introduced Base Changes and New Restriction Sites: (sequence starts at nt 3954)

```
 I  A  A  A  N  S  S  I  N  I  A  S  V  G  T  L  Y
ATAGCCGCAGCTAACAGCTCCATAAACATAGCTAGTGTGGGTACTCTTTAT
          ⬇                                  ⬇
        CTGCAG                              GGTACC
         Pst I                               Kpn I
```

FIG. 10(b)

Series of Sequences to be Inserted Between the Restriction Sites to Insert the MUC1(16) Epitope at Various Locations.

```
    G   V   T   S   A   P   D   T   R   P   A   P   G   S   T   A
   GGTGTTACTTCTGCTCCTGATACTAGACCTGCTCCTGGTTCTACTGCT
   CCACAATGAAGACGACCACTATGATCTGGACGAGGACCAAGATGACGA
   ⬅──────────────────────────────⟶
```

| | |
|---|---|
| GCTAACAGC | TCCATAAACATAGCTAGTGTGGGTAC |
| ACGTCGATTGTCG | AGGTATTTGTATCGATCACACC |
| | |
| GCTAACAGCTCC | ATAAACATAGCTAGTGTGGGTAC |
| ACGTCGATTGTCGAGG | TATTTGTATCGATCACACC |
| | |
| GCTAACAGCTCCATA | AACATAGCTAGTGTGGGTAC |
| ACGTCGATTGTCGAGGTAT | TTGTATCGATCACACC |
| | |
| GCTAACAGCTCCATAAAC | ATAGCTAGTGTGGGTAC |
| ACGTCGATTGTCGAGGTATTTG | TATCGATCACACC |
| | |
| GCTAACAGCTCCATAAACATA | GCTAGTGTGGGTAC |
| ACGTCGATTGTCGAGGTATTTGTAT | CGATCACACC |
| | |
| GCTAACAGCTCCATAAACATAGCT | AGTGTGGGTAC |
| ACGTCGATTGTCGAGGTATTTGTATCGA | TCACACC |

FIG. 11

Lipman-Pearson alignment of RCNMV and TBSV coat protein sequences.

```
Lipman-Pearson Protein Alignment
Ktuple: 2;  Gap Penalty: 4;  Gap Length Penalty: 12
Seq1(1>389)     Seq2(1>340)     Similarity    Gap        Gap        Consensus
tbsvtbs.PRO     rcnmvdia.PRO    Index         Number     Length     Length
(64>387)        (8>338)         26.9          4          7          331

↱70       ↱80       ↱90       ↱100      ↱110      ↱120
     KKQQMINHVGGTGGAIMAPVAVTROLVGSKPKFTGRTSGSVTVTHREYLSQVNNSTGFQV
     K.:Q. :. . T .: : .VA:. .         . ... : .: H : : V .S. .:.
     KSKQRSQPRNRTPNTSVKTVAIPFAKTQIIKTVNPPPKPARGILHTQLVMSVVGSVQMRT
        ⊥10       ⊥20       ⊥30       ⊥40       ⊥50       ⊥60

↱130      ↱140      ↱150      ↱160      ↱170      ↱180
     NGGIVGNLLQLNPLNGTLFSWLPAIASNFDQYTFNSVVLHYVPLCSTTEVGRVAIYFDKD
     N.G  .: ::LNP N :LF: L: A:N:D Y ::.:.L:YVPL :.. : GRVA: .D D
     NNGKSNQRFRLNPSNPALFPTLAYEAANYDMYRLKKLTLRYVPLVTVQNSGRVAMIWDPD
        ⊥70       ⊥80       ⊥90       ⊥100      ⊥110      ⊥120

↱190      ↱200      ↱210      ↱220      ↱230      ↱240
     SEDPEPADRVELANYSVLKETAPWAEAMLRVPTDKIKRFCDDSSTSDHKLIDLGQLGIAT
     S:D:.P..R E::.YS  .TA ... L :P:D: RF .D::T D:KL:D:GQL :.T
     SQDSAPQSRQEISAYSRSVSTAVYEKCSLTIPADNQWRFVADNTTVDRKLVDFGQLLFVT
        ⊥130      ⊥140      ⊥150      ⊥160      ⊥170      ⊥180

↱250      ↱260      ↱270      ↱280      ↱290        ↱300
     YGGAGTNAVGDIFISYSVTLYFPQPTNTLLSTRRLDLAGALVTASGPGYLLVSR---TAT
     .:G::.  ..GDIF:...V.:  PQPT.::: .   :DL:G:L:. .GP:YL: :    T::
     HSGSDGIETGDIFLDCEVEFKGPQPTASIVQKTVIDLGGTLTSFEGPSYLMPPDAFITSS
        ⊥190      ⊥200      ⊥210      ⊥220      ⊥230      ⊥240

↱310      ↱320      ↱330      ↱340      ↱350
     VLTMTFRATGTFVISGTYRCLTATTLGLAG--GVNVNSITVVDNIG-TDSAFFINCTVSN
     :.: .:GT:::: .   C T:.:.:.:G  .:  :: . :: ..S  F.:..V :
     SFGLFVDVAGTYLLTLVVTCSTTGSVTVGGNSTLVGDGRAAYGSSNYIASIVFTSSGVLS
        ⊥250      ⊥260      ⊥270      ⊥280      ⊥290      ⊥300

↱360      ↱370      ↱380
     LPSVVTFT-STGITSATVHCVRATRQNDVSL
     .: V F: S:G:.. ::  R .: N   L
     TTPSVQFSGSSGVSRVQMNICRCKQGNTFIL
        ⊥310      ⊥320      ⊥330
```

Beta plot - Chou-Fasman

FIG. 14(a)

Sequence of RCNMV Coat Protein Spanning The Potential Insertion Site With Introduced Base Changes and New Restriction Sites: (sequence starts at nt 3070)

```
S   I   V   Q   K   T   V   I   D   L   G   G   T   L   T   S   F
AGCATCGTACAGAAAACTGTAATTGATCTCGGTGGGACACTCACTTCTTTC
            ↓   ↓                              ↓   ↓
            GTGCAC                              GTTAAC
            ApaLI                               HpaI
```

FIG. 14(b)

Series of Sequences to be Inserted Between the Restriction Sites to Insert the MUC1(16) Epitope at Various Locations

```
    G   V   T   S   A   P   D   T   R   P   A   P   G   S   T   A
    GGTGTTACTTCTGCTCCTGATACTAGACCTGCTCCTGGTTCTACTGCT
    CCACAATGAAGACGACCACTATGATCTGGACGAGGACCAAGATGACGA
   ←                                                              →
```

| | |
|---|---|
| GAAAACTGTA | ATTGATCTCGGTGGGACGTT |
| ACGTCTTTTGACAT | TAACTAGAGCCACCCTGCAA |
| | |
| GAAAACTGTAATT | GATCTCGGTGGGACGTT |
| ACGTCTTTTGACATTAA | CTAGAGCCACCCTGCAA |
| | |
| GAAAACTGTAATTGAT | CTCGGTGGGACGTT |
| ACGTCTTTTGACATTAACTA | GAGCCACCCTGCAA |
| | |
| GAAAACTGTAATTGATCTC | GGTGGGACGTT |
| ACGTCTTTTGACATTAACTAGAG | CCACCCTGCAA |
| | |
| GAAAACTGTAATTGATCTCGGT | GGGACGTT |
| ACGTCTTTTGACATTAACTAGAGCCA | CCCTGCAA |
| | |
| GAAAACTGTAATTGATCTCGGTGGG | ACGTT |
| ACGTCTTTTGACATTAACTAGAGCCACCC | TGCAA |

CHIMAERIC PLANT VIRUSES WITH MUCIN PEPTIDES

All documents cited herein are incorporated by reference in their entirety.

TECHNICAL FIELD

This invention is in the field of vaccination, more particularly cancer vaccines. It relates to antigenic materials peptides which are rendered more antigenic by being presented on carrier virus particles. The peptides are able to induce antibodies to tumour antigens.

BACKGROUND ART

Based on the success of vaccines for the treatment and prevention of infectious diseases, there have been attempts over the years to develop cancer vaccines. Early attempts at cancer vaccines were based on immunising the cancer patient with killed tumour cells together with adjuvant.

Further development of cancer vaccines has focused on directing the immune response to identified tumour antigens present on the surface of tumour cells. The advent of monoclonal antibodies enabled the identification of so-called "tumour-specific" antigens. Typically, however, tumour antigens not tumour-specific, but are over-expressed on tumour cells and rarely expressed, or under-expressed, on normal cells.

A well-characterised tumour antigen is "polymorphic epithelial cell mucin" (PEM), the product of the MUC1 gene. PEM is over-expressed and aberrantly glycosylated in many carcinomas (breast, pancreas, ovary, lung, urinary bladder, prostate, and endometrium) thus resulting in cancer cells expressing antigenically-distinct PEM molecules on their surface. Both humoral and cellular immune responses specific to PEM have been detected in cancer patients. These properties make PEM particularly well-suited to act as a target molecule for cancer immunotherapy. In addition, the over-expression of mucin on tumour cells suggests that the mucin may be important for the maintenance of the tumour. Such over-expression of mucin would alleviate potential problems of tumour cells escaping immunotherapy by down-regulating the MUC1 gene. U.S. Pat. Nos. 4,963,484 & U.S. Pat. No. 5,053,489 and international patent application WO88/05054 describe the purification of human mucin, the isolation of monoclonal antibodies thereto, the cloning of cDNAs coding for human mucin, and the use of these for diagnostic and therapeutic applications.

Zhang et al. [*Cancer. Res.* (1996) 56:3315–3319] disclose the preparation of several MUC1 peptide vaccines and compares their immunogenicity. Vaccines comprising adjuvant and a MUC1 peptide covalently linked to the protein carrier KLH achieved greatest immunogenicity. The authors concluded that MUC1 peptides of 30 or more amino acids are better immunogens than MUC1 peptides of 20 amino acids.

The MUC1 gene product is a high molecular weight (MW>200 kDa) transmembrane glycoprotein expressed on the apical surface of many simple epithelial cells. It has a relatively large extracellular domain varying from 1000 to 2200 amino acids and a cytoplasmic tail of 69 amino acids. The extracellular domain consists mainly of tandem repeats of the 20 amino acid sequence PDTRPAPGSTAPPAHGVTSA, set forth as SEQ ID NO:1 [for a review, see Apostolopoulos & McKenzie (1994) *Crit. Rev. Immunol.,* 14: 293–309]. Variability in the number of repeats accounts for the variability in the size of the extracellular domain. Each repeat contains five potential O-linked glycosylation sites and two or possibly three of these sites are believed to be utilised.

The aberrant glycosylation of PEM observed in a variety of cancers is due to alterations in the activity of glycosyltransferases with some transferases being inactive and the activity of others being increased. Abnormal glycosylation of PEM in cancer cells leads to three types of cancer-associated epitopes: (a) peptides, from the core protein, that are exposed following under-glycosylation; (b) "new" carbohydrates resulting from deficient and aberrant glycosylation; and (c) "new" glycopeptides resulting from deficient and aberrant glycosylation.

Many different approaches have been considered as potential cancer vaccines aimed at inducing a beneficial immune response directed towards PEM-expressing tumour cells. These include: cells expressing mucins: mucin purified from cancer cells; mucin core protein produced as a recombinant protein; different mucin glycoproteins produced by transfected cells; peptide or glycopeptide based on the tandem repeat; recombinant animal viruses expressing portions of the MUC1 cDNA gene product; synthetic carbohydrates based on short aberrant chains present on mucins on cancer cells; naked MUC1 DNA; and anti-MUC1 antibodies.

Of these, anti-MUC1 antibodies, synthetic carbohydrates, recombinant animal viruses, and peptides based on the tandem repeat have been developed sufficiently to reach evaluation in clinical trials. However, one significant problem with all of the above approaches is that a poor and/or inadequate immune response towards mucin-expressing tumour cells is observed.

It is an object of the present invention to alleviate this problem by providing an effective means for presenting a peptide of a tumour-associated mucin.

DISCLOSURE OF THE INVENTION

According to a first aspect of the invention, there is provided a chimaeric virus particle (CVP) derived from a plant virus, having a coat protein with a beta-barrel structure, and modified by insertion of an immunogenically active peptide of a tumour-associated mucin at an immunogenically effective site in the coat protein.

These CVPs provide, inter alia, two main advantages over the above-identified prior art antigen-presenting means. Firstly, conventional live animal virus vectors (as carriers) can be dispensed with. Secondly, the need for separate mucin peptide synthesis and the need for time-consuming chemical-coupling thereof to a conventional carrier, such as keyhole limpet haemocyanin (KLH), can be avoided. In addition, the CVPs have been shown to induce good mucosal immunity (e.g. when administered intranasally), they are superior to the 'standard' of presentation by conjugation to KLH [Zhang et al., supra], they do not require the addition of exogenous adjuvants to induce a strong immune response, and show good Th1 bias.

It has been found that surprisingly superior immunogenicity to a mucin antigen can be obtained by presenting a mucin peptide in a composite particle derived from certain plant viruses. The plant viruses especially useful for the purposes of the present invention are those having a coat protein with a β-barrel structure containing loops between β-sheets. Composite virus particles of this general type and the methods of constructing such particles are disclosed in international patent applications WO92/18618 and WO96/02649.

An advantage of the use of viruses which have a β-barrel structure is that the loops between the individual strands of β-sheet provide convenient sites for the insertion of mucin peptides. Modification of one or more loops is a preferred strategy for the expression of mucin peptides in accordance with the present invention. These viruses include all members of the following virus families: Caulimoviridae, Broinoviridae, Comoviridae, Geminiviridae, Reoviridae, Partitiviridae, Sequiviridae, Tombusviridae, and the following virus genera: Luteovirus, Marafivirus, Sobemovirus, Tymovirus, Enamovirus and Idaeovirus. Of the Tombusviridae family, the following genera are mentioned in particular: Dianthovirus, Machlomovirus and Necrovirus. An advantage of the Comoviridae and Sequiviridae is that their capsid contains sixty copies each of 3 different β-barrels which can be individually manipulated. All other virus families and genera listed above have similar 3-dimensional structures but with a single type of β-barrel. Viruses selected from the family Comoviridae (e.g. cowpea mosaic virus and bean pod mottle virus) are particularly preferred, with CPMV being the most preferred virus.

The invention can be applied to any plant virus having a coat protein with a β-barrel structure. In a preferred embodiment the three dimensional structure of a plant virus is examined in order to identify portions of a coat protein which are particularly exposed on the virus surface and which are therefore potentially optimum sites for insertion. In a further embodiment the amino acid sequence of the exposed portions of a coat protein is examined for amino acids which break α-helical structures because these are potentially optimum sites for insertion. Examples of suitable amino acids are proline and hydroxyproline, both of which whenever they occur in a polypeptide chain interrupt the α-helix and create a rigid kink or bend in the structure.

All plant viruses possessing icosahedral symmetry whose structures have been solved conform to the eight stranded β-barrel fold as exemplified by CPMV, and it is likely that this represents a common structure in all icosahedral viruses. All such viruses are suitable for use in this invention for the presentation of foreign peptide sequences in the loops between the β-strands.

To date, viruses from nine plant virus genera and three subgroup 2 ssRNA satellite viruses have had their tertiary and quaternary structures solved at high resolution. These are:

| Name | Acronym | Genus | Family |
|---|---|---|---|
| Southern bean mosaic virus | SBMV | *Sobemovirus* | not assigned |
| Sesbania mosaic virus | SMV | *Sobemovirus* | not assigned |
| tomato bushy stunt virus | TBSV | *Tombusvirus* | *Tombusviridae* |
| turnip crinkle virus | TCV | *Carmovirus* | *Tombusviridae* |
| cowpea chlorotic mottle virus | CCMV | *Bromovirus* | *Bromoviridae* |
| alfalfa mosaic virus | AMV | *Alfamovirus* | *Bromoviridae* |
| bean pod mottle virus | BPMV | *Comovirus* | *Comoviridae* |
| cowpea mosaic virus | CPMV | *Comovirus* | *Comoviridae* |
| red clover mottle virus | RCMV | *Comovirus* | *Comoviridae* |
| tobacco ringspot virus | TRSV | *Nepovirus* | *Comoviridae* |
| turnip yellow mosaic | TYMV | *Tymovirus* | not assigned |
| tobacco necrosis virus | TNV | *Necrovirus* | *Tombusviridae* |
| satellite tobacco necrosis virus | | | Subgroup 2 |
| satellite panicum mosaic virus | | | Subgroup 2 |
| satellite tobacco mosaic virus | | | Subgroup 2 |

The similarity of the secondary structural elements and their spatial organisation is illustrated in FIG. 1. Any of the loops which lie between the β-strands can be used for insertion of foreign epitopes, but the insertions are made such that the additions are exposed on either the internal or external surface of the virus and such that assembly of the coat protein subunits and the infectivity of the virus are not abolished. The choice of a particular loop can be made using knowledge of the structure of individual coat protein subunits and their interactions with each other, as indicated by the crystal structure, such that any insertions are unlikely to interfere with virus assembly. The choice of precise insertion site can be made, initially, by inspection of the crystal structure, followed by in vivo experimentation to identify the optimum site.

The present invention is also applicable to those β-barrel containing plant viruses whose crystal structures have not yet been determined. Where significant sequence homology within the coat protein genes exists between one virus whose crystal structure is unknown and a second virus whose crystal structure has been determined, alignment of the primary structures will allow the locations of the loops between the β-strands to be inferred [Dolja & Koonin (1991) *J. Gen. Virol.* 72:1481–1486]. In addition, where a virus has only minimal coat protein sequence homology to those viruses whose crystal structure has been determined, primary structural alignments may be used in conjunction with appropriate secondary and tertiary structural prediction algorithms to allow determination of the location of potential insertion sites.

CPMV comprises two subunits, the small (S) and the large (L) coat proteins, of which there are 60 copies of each per virus particle. Mucin peptide sequences may be expressed on either the L or S proteins or on both coat proteins on the same virion. Thus, up to 120 copies of the mucin peptide sequence may be expressed on a single virus particle.

A 3.5 Å electron density map of CPMV (see FIG. 1 in WO92/18618) shows the clear structural relationship between the capsids of CPMV and the T=3 plant viruses, for example the bromoviruses (in particular CCMV) and the sobemoviruses (in particular SBMV). The capsids of these latter viruses are composed of 180 identical coat protein subunits, each consisting of a single β-barrel domain. These domains can occupy three different positions, namely A, B and C, within the virions (see FIG. 1 in WO92/18618). The two coat proteins of CPMV were shown to consist of three distinct β-barrel domains, two being derived from the large capsid protein and one from the small capsid protein. Thus, in common with the T=3 viruses, each CPMV particle is made up of 180 β-barrel structures. The single domain from the small subunit occupies a position analogous to that of the A type subunits of CCMV and SBMV and other viruses, whereas the N- and C-terminal domains of the large capsid protein occupy the positions of the C and B type subunits respectively (see FIG. 1 in WO92/18618).

X-ray diffraction analysis of crystals of CPMV and BPMV shows that their 3-D structures are very similar and are typical of the Comoviridae in general.

In the structures of CPMV and BPMV, each β-barrel consists principally of 8 strands of antiparallel β-sheet connected by loops of varying length. The connectivity and nomenclature of the strands is given in FIG. 2 of WO92/18618. The flat β-sheets are named the B,C,D,E,F,G,H and I sheets, and the connecting loops are referred to as the βB–βC, βD–βE, βF–βG and βH–βI loops.

One difference between the Comoviridae and the animal Picornaviridae is that the protein subunits of Comoviridae lack the large insertions between the strands of the β-barrels found in Picornaviridae. The four loops (βB–βC, βD–βE, βF–βG and βH–βI—see FIG. 3 in WO92/18618) between the β-sheets are suitable for expression of tumour-associated mucin peptide sequences.

The βB–βC loop in the small capsid protein is particularly preferred as the insertion site. This loop has an engineered AatII. site and a unique NheI site at position 2708 of the M RNA-specific sequence where mucin peptide sequences may be inserted (see FIG. 4 of WO92/18618). The insertion site immediately preceding Pro²³ in the βB–βC loop of the small capsid protein is most preferred.

To demonstrate the present invention, the plant virus CPMV in particular has been primarily chosen.

Various sites in the CPMV coat protein have been identified as suitable for insertion of the foreign peptide. The co-ordinates given below refer to the linear amino acid sequence of the CPMV coat protein (S or L subunit).

Any insertion site which does not lie between the N-terminus of a subunit and a β-strand, or between a β-strand and the C-terminus, is considered to lie between two β-strands. Such an insertion site may lie in a short loop at one of the axes of symmetry of the virus or in one of the much longer connecting strands which form the body of the protein subunits and which may contain additional secondary structure and form loops on the surface of the virus. In particular, there are α-helices present in some of the connecting strands which form the body of the protein subunits, and the co-ordinates given for some of the insertion sites may indicate that an α-helix is present between the insertion site and the preceding or proceeding β-strand. For example, the S protein C' and C" β-strands represent a secondary structure formed in the loop between the βC and βD strands.

(i) External Surface Sites

S Subunit (A Domain) Insertion Sites

βB–βC: The residue between the β-strands are Thr 19 to Val 2, and the preferred insertion site is between amino-acids 22 and 23. Insertion sites either side of this are also suitable, notably between residues 21 and 22.

βC'–βC": The residues between the β-strands are Val 42 to Asn 46.

βH–βI: This site is at the tip of the five-fold axis and the residues between the β-strands are Thr 152 to Gln 158.

βD–βE: Again, this site is at the tip of the five-fold axis and the residues between the β-strands are Ala 80 to Gln 90.

βE–βF: This site is not at the tip of the five-fold axis, but lies 'behind' and to one side of the β-strands. The residues between the β-strands are Arg 96 to Ala 106. Residues 98 to 102 are preferred.

L Subunit (B Domain) Insertion Sites

The B domain of the L subunit comprises ammo acids 183–374 of the linear amino-acid sequence.

βB–βC: This site is in the equivalent location on the subunit to the standard S protein insertion site and is at the three-fold axis of the virus. The residues between the β-strands are Pro201 to Glu209.

βH–βI: Again this site is at the three-fold axis of the virus and the residues between the β-strands are His331-Asp341.

βC–αA (βC–βD): This site lies between the βC and βD strands. The protein chain loops out to form part of the body of the protein domain. Within this loop is an α-helix (termed αA) the insertion site is a surface exposed portion which lies between the βC strand and the αA helix. The surface exposed residues are Ala 223 to Ala226.

βG–αD (βG–βH): This site lies between the βG and βH strands. The protein chain loops out to form part of the body of the protein domain. Within this loop is an α-helix (termed αD) and the insertion site is a surface portion which lies between the αD helix and βH strands which are surface exposed. The surface exposed residues are Pro314 to Thr317.

βE–αB (βE–βF): This site lies between the βE and βF strands. The protein chain loops out to form part of the body of the protein domain. Within this loop is an α-helix (termed αβ) and the insertion site is a surface portion which lies between the βE strand and the αB helix. The surface exposed residues are Gly269 to Phe275.

L subunit (C Domain) Insertion Sites

The C Domain of the L Subunit comprises amino-acids 1–182 of the linear amino-acid sequence.

βE–αB (βE–βF): This site lies between the βE and βF strands. The protein chain loops out to form part of the body of the protein domain. Within this loop is an α-helix (termed αB) and the insertion site is a surface exposed portion which lies between the βE strand and the αB helix. The surface exposed residues are Gly95 to Thr102.

αD–βH (βG–βH): This site lies between the βG and βH strands. The protein chain loops out to form part of the body of the protein domain. Within this loop is an α-helix (termed αD) and the insertion site is a surface portion which lies between the αD helix and the βH strands. The surface exposed residues are Ser142 and Arg145.

β–αA (βC–βD): This site lies between the βC and βD strands. The protein chain loops out to form part of the body of the protein domain. Within this loop is an α-helix (termed αA) and the insertion site is a surface exposed portion which lies between the βC strand and the αA helix. The surface exposed residues, not part of any secondary structural element, are Gly53 to Phe56.

βB–βC: This site is an equivalent location on this domain to the S protein βB–βC (identified above) insertion site and is at the three-fold axis of the virus. The residues between the β-strands are Ser33 to Leu42.

(ii) Internal Surface Sites

S Subunit (A Domain) Insertion Sites

β–G–βH: This protein chain between β-strands points in towards the interior of the virus and forms a 'double loop'. One insertion site comprises residues Pro128 to Ser130.

L Subunit (B Domain) Insertion Sites

βF–βG: This loop is at the three-fold axis symmetry of the virus, and is the bottom loop of the four. The residues in the loop are Gln287 to Glu293.

C Domain β1–B Domain βB: This is the junction between the B and C domains of the L subunit. This linker sequence comprises residues Asn374 to Asp186. The insertion site is around Ala185, which is assigned to the B domain.

L Subunit (C Domain) Insertion Sites

βG–αD (βG–βH): This site lies between the βG and βH strands. The protein chain loops out to form part of the body of the protein domain. Within this loop is an α-helix (termed αD) and the insertion site is an internal projecting loop which lies between the βG strands and the αD helix. The residues in this loop are Asn130 to Ser135.

The RNA or DNA encoding the mucin peptide may be inserted into the plant virus genome in a variety of configurations. For example, it may be inserted as an addition to the existing nucleic acid or as a substitution for part of the existing sequence, the choice being determined largely by the structure of the capsid protein and the ease with which additions or replacements can be made without interference with the capacity of the genetically-modified virus to assemble. Determination of the permissible and most appropriate size of addition or deletion for the purposes of this invention may be achieved in each particular case by experiment in the light of the present disclosure. The use of addition inserts appears to offer more flexibility than replacement inserts in some instances.

The mucin peptides which may be incorporated into plant viruses according to this invention may be of highly diverse types and are subject only to the limitation that the nature and size of the peptide and the site at which it is placed on or in the virus particle do not interfere with the capacity of the modified virus to assemble when cultured in vitro or in vivo. The peptide preferably contains 5 or more amino acids.

The following are preferred mucin peptides sequences for forming CVPs in accordance with the present invention. Optionally repeating sequences of the 20 amino acid sequence "PDTRPAPGSTAPPAHGVTSA" (SEQ. ID No.1) are preferred. An optionally repeating partial sequence of the above 20 amino acid sequence is particularly preferred. In this respect the peptide sequences "PDTRP" (SEQ. ID No.2) and "APDTR" (SEQ. ID No.3) are particularly preferred, as are the mimetic peptide sequences: "DAHWESWL" (SEQ. ID No.4) and "DLHWASWV" (SEQ. ID No.5).

The mucin peptide may be of the general formula "$(aa)_x$ PDTRP$(aa)_y$" (SEQ ID NO:2) or "$(aa)_x$APDTR$(aa)_y$" (SEQ ID NO:3) where aa is an amino acid residue, the same or different in each position, x is an integer from 0 to 1000, and y is an integer from 0 to 1000. Preferably x is an integer from 0 to 500, more preferably 0 to 100, most preferably 0 to 10, and y is an integer from 0 to 500, more preferably 0 to 100, most preferably 0 to 10.

It is most preferred that the sequence "PDTRP" (SEQ ID NO:2) or "APDTR" (SEQ ID NO:3) is located towards the middle of the mucin peptide sequence of interest (as for example in the MUC1(16) defined hereinafter). Alternatively, the peptide sequence "PDTRP" (SEQ ID NO:2) or "APDTR" (SEQ ID NO:3) may be located towards the beginning of the mucin peptide sequence of interest (as for example in the MUC1(23) defined hereinafter). The above sequences/partial sequences are based on the 20 amino acid tandem repeat sequence of the extracellular domain of PEM.

According to a second aspect of the invention, there is provided a method of producing a chimaeric virus particle which comprises introducing a nucleotide sequence coding for a tumour-associated mucin peptide to modify the plant viral nucleic acid which codes for the coat protein, infecting plants, plant tissue, plant cells, or protoplasts with the modified viral nucleic acid, and harvesting chimaeric virus particles. The introduced nucleotide sequence is preferably inserted in that part of the plant viral nucleic acid which codes for an exposed region of the coat protein.

This procedure is best carried out by direct manipulation of the DNA of the virus in the case of DNA viruses or by manipulation of the cDNA corresponding to the RNA of an RNA virus. In the case of an RNA virus, the modified cDNA or an RNA transcript thereof is prepared for inoculation of plant cells or preferably whole plants so as to achieve a multiplication stage prior to the harvesting of assembled particles of the modified virus. In the case of a DNA virus, the DNA itself is introduced into the plant. In this way, the mucin peptide is initially expressed as part of the capsid protein and is thereby produced as part of the whole virus particle.

In order to produce modified virus on a commercial scale, it is not necessary to prepare infective inoculant (DNA or RNA transcript) for each batch of virus production. Instead, an initial inoculant may be used to infect plants and the resulting modified virus may be passaged in the plants to produce whole virus or viral RNA as inoculant for subsequent batches.

Preferably the method is applied to an RNA plant virus, in which case the method comprises introducing a DNA coding for the tumour-associated mucin peptide into a cDNA corresponding to the RNA of the plant virus which codes for an exposed portion of its coat protein, inoculating plants, plant tissue, plant cells, or protoplasts with the thus modified cDNA or an RNA transcript thereof, if necessary together with any other DNA or RNA required for multiplication and assembly of whole virus particles in the plant material, and harvesting chimaeric virus particles. More preferably, the modified cDNA is produced by introducing the DNA encoding the mucin peptide into a DNA fragment excised from the plant viral cDNA, and reinserting the modified excised fragment so as to constitute the plant viral cDNA in modified form.

According to a third aspect of the invention, there is provided a vaccine comprising CVPs, as hereinbefore described, as an immunogenic component thereof. The vaccine may further comprise adjuvant, for example Freund's complete adjuvant (FCA), QuilA, QS-21, ISCOM matrix, algammulin, alum, or combinations thereof. QS-21 is preferred. Alternatively, adjuvant may be omitted from the vaccine. It is particularly surprising that the chimaeric virus particles of the present invention are strongly immunogenic in the absence of an adjuvant (e.g. see Examples 7 & 8).

Vaccines according to the present invention are particularly suited for nasal administration. For comparison purposes, a chimaeric plant virus particle comprising alfalfa mosaic virus coat protein and a rabies virus peptide is described in Modelska et al. [*PNAS USA* (1998) 95:2481–85]. The chimeric plant virus coat protein assembled in planta into virus-like particles which (in contrast to the CVPs of the present invention) were non-infectious to plants. Three doses of 50 μg of the virus-like particles were required to obtain an immune response when administered to mice by injection in the absence of an adjuvant. In contrast, a strong immune response was achieved in accordance with the present invention by either subcutaneous or nasal administration to mice of two 100 μg doses of CPMV-MUC1(16) in the absence of an adjuvant (see Examples 7 & Example 8). The nasal vaccines of the invention may be adapted for intranasal administration, such as by nasal spray, nasal drops, gel or powder [Almeida & Alpar (1996) *J. Drug Targeting* 3:455–467].

BRIEF DESCRIPTION OF DRAWINGS

FIG. 2 shows CPMV-specific and MUC1-60mer-specific IgG1/IgG2a values following immunisation with CVPs of the invention. FIG. 2A shows data using MUC1 (16), 2B shows data using MUC1(23), and 2C shows control data using wild type CPMV. Titres are expressed as end-point titres obtained with sera from individual mice. Results are of a single experiment representative of a further two experiments.

FIG. 3A shows the extent of staining of tumour cells by serum from mice immunized with CVPs in Freund's complete adjuvant (FCA), while FIG. 3B shows the extent of staining of tumour cells by serum from mice immunized with CVPs in QS-21. Results are expressed as mean fluorescence intensity (MFI).

FIG. 4 compares the induction of MUC1-specific antibodies by CVPs with the MUC1(16) insert or by the MUC1 peptide conjugated to KLH. Results are expressed as mean end-point titres (standard deviations shown) obtained with sera from individual mice.

FIG. 7 shows serum $IgG_1/IgG_{2a}$(7A) and lavage IgA (7B) titres, comparing values with and without CT adjuvant in intranasal immunisation. 7C shows results using ISCOMs as intranasal adjuvant. Titres for each mouse are expressed as end-point titres obtained from individual mice.

FIG. 8A shows the nucleotide (SEQ ID NO:8) and protein (SEQ ID NO:9) sequences of the SBMV coat protein (starting at nucleotide 3955) spanning a potential insertion site. The bold nucleotides show base changes used to introduce new restriction sites. FIG. 8B shows the nucleotide (SEQ ID NO:10) and protein (SEQ ID NO:6) sequences of MUC1(16), as well as a series of sequences to be inserted between the restriction sites of the SBMV coat protein. In the five constructs shown, the MUC1(16) epitope sequence is inserted between SBMV coat protein amino acids 251–252 (SEQ ID NO:11), 252–253 (SEQ ID NO:12), 253–254 (SEQ ID NO:13), 254–255 (SEQ ID NO:14), and 255–256 (SEQ ID NO:15).

FIG. 9 shows a comparison of the βH–βI loop of three sobemoviruses: LTSV (SEQ ID NO:16); SBMV (SEQ ID NO:17); and SMV (SEQ ID NO:18). Conserved resides are highlighted in bold and the locations of the loops (=) and β-strands (#) are indicated.

FIG. 10A shows the nucleotide (SEQ ID NO:19) and protein (SEQ ID NO:20) sequences of the LTSV coat protein (starting at nucleotide 3954) spanning a potential insertion site. The bold nucleotides show base changes to introduce new restriction sites. FIG. 10B shows the nucleotide (SEQ ID NO:10) and protein (SEQ ID NO:6) sequences of MUC1 (16), as well as a series of sequences to be inserted between the restriction sites of the LTSV coat protein. In the six constructs shown, the MUC1(16) epitope sequence is inserted between LTSV coat protein amino acids 218–219 (SEQ ID NO:21), 219–220 (SEQ ID NO:22), 220–221 (SEQ ID NO:23), 221–222 (SEQ ID NO:24), 222–223 (SEQ ID NO:25), and 223–224 (SEQ ID NO:26).

FIG. 11 shows a Lipman-Pearson alignment of the coat protein sequences of RCNMV (SEQ ID NO:28) and TBSV (SEQ ID NO:27).

FIG. 13 shows the application of the EMBL PHDsec algorithm program to part of the RCNMV (SEQ ID NO:30) sequence. "AA" shows the amino acid sequence; "PHD sec" indicates "profile network prediction Heidelberg" of secondary structure, with "H" indicating helix and "E" indicating extended (sheet); "Rel sec" indicates the reliability index of the prediction; "prH", "prE" and "prL" indicate the probability for assigning a helix, strand or loop; "SUB" indicates a subset of the prediction, for all residues with an average expected accuracy of >82%.

FIG. 14A shows the nucleotide (SEQ ID NO:31) and protein (SEQ ID NO:32) sequences of the RCNMV coat protein (starting at nucleotide 3070) spanning a potential insertion site. The bold nucleotides show base changes to introduce new restriction sites. FIG. 14B shows the nucleotide (SEQ ID NO:10) and protein (SEQ ID NO:6) sequences of MUC1(16), as well as a series of sequences to be inserted between the restriction sites of the RCNMV coat protein. In the six constructs shown, the MUC1(16) epitope sequence is inserted between RCNMV coat protein amino acids 221–222 (SEQ ID NO:33), 222–223 (SEQ ID NO:34), 223–224 (SEQ ID NO:35), 224–225 (SEQ ID NO:36), 225–226 (SEQ ID NO:37), and 226–227 (SEQ ID NO:38).

MODES FOR CARRYING OUT THE INVENTION

Background Experimental Details

Figure 1:
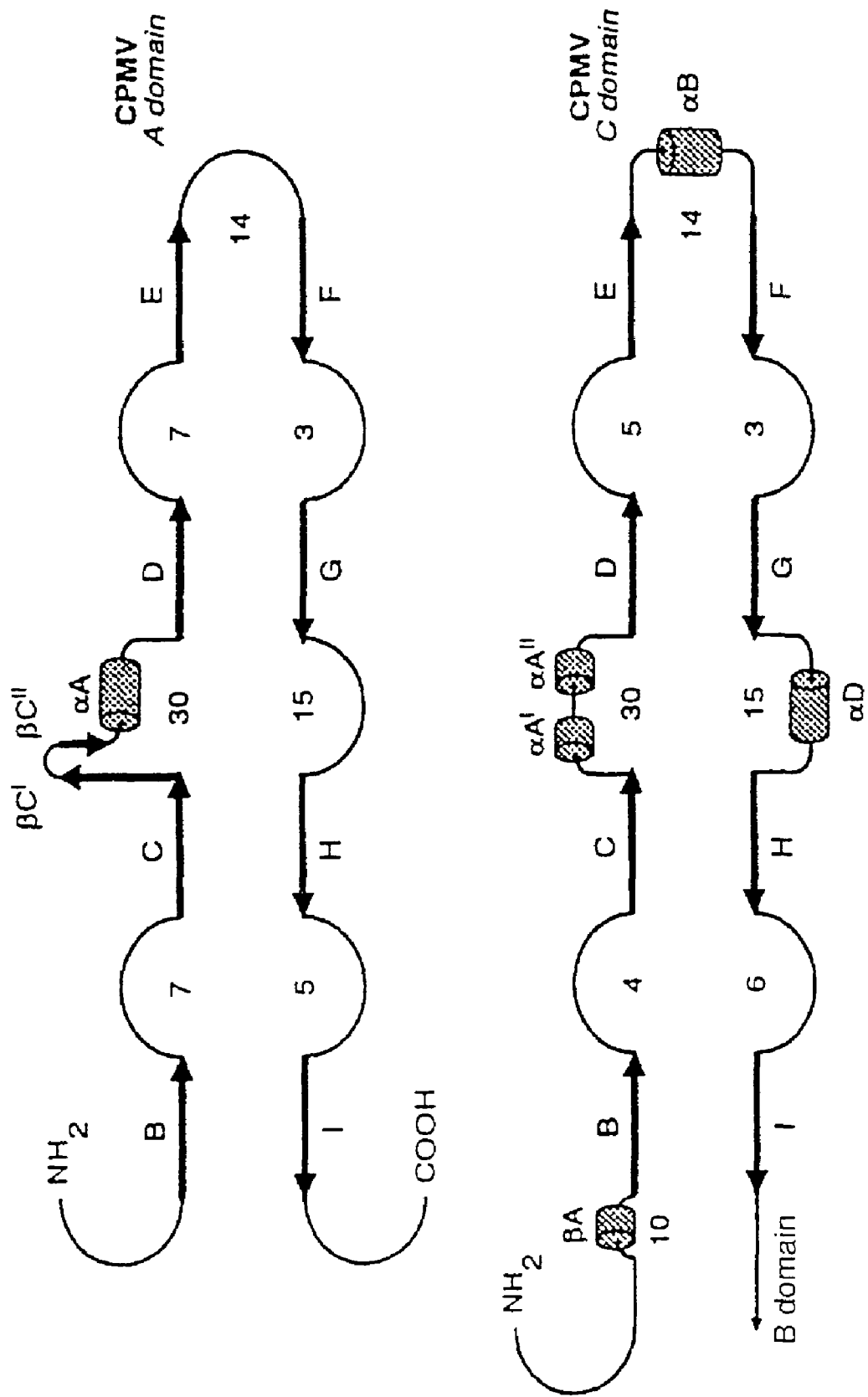
FIG. 1 is a simple line drawing of all the solved β-barrel containing virus structures showing the secondary structural elements which make up the coat protein domains.

In Examples 1–9, either a 16mer or a 23mer peptide sequence derived from the MUC1 gene product tandem repeat was expressed in the βB–βC loop of CPMV S protein. The corresponding CVPs are known herein as CPMV-MUC1(16) and CPMV-MUC1(23), respectively. The CVPs were used to immunise mice and the MUC1-specific immune response was examined. The CVPs were shown to be highly efficient carriers of the MUC1 peptide sequences, eliciting high titres of anti-MUC1 antibodies that strongly recognised MUC1-bearing tumour cells and fresh breast tissue. Mucin-based CVPs therefore have significant potential as cancer vaccines against mucin-expressing epithelial cancers.

Experimental Animals. Female C57BL/6 mice and C57BL6xSacII MUC1-transgenic mice (both H-2$^b$), aged 6–8 weeks, were used in these studies.

Monoclonal antibodies (mAbs) and cell lines. HMFG2 is a MUC1-specific mouse IgG1 mAb [Burchell et al. (1983) J. Immunol. 131:508–513]. E4 cells are derived from the murine (BALB/c) mammary epithelial cancer cell line 410.4 transfected with the MUC1 gene. T47D is a human breast carcinoma cell line, obtained from ATCC.

ELISA for detection of MUC1-specific antibody. ELISAs for the detection of MUC1-specific and CPMV-specific antibody in sera was performed as described by Porta et al. [Virology (1994) 202:949–955] and Usha et al. [Virology (1993) 197:366–374]. For the detection of anti-MUC1 antibody, the wells of 96-well ELISA plates (Dynatech Immulon-4) were coated with 0.1 μg/well streptavidin for 1 hr at 37° C. followed by 0.1 μg/well of biotinylated MUC1 60-mer peptide for 1 hr at 37° C. For the detection of anti-CPMV antibody, the wells were coated directly with 0.1 μg/well of CPMV for 1 hr at 37° C. A series of doubling dilutions of serum were incubated on the antigen-coated plates for 1 and 4 hr respectively at 37° C. Bound antibody was detected with alkaline phosphatase conjugated goat anti-mouse IgG1 and IgG2a (a mix of the two conjugates) or with IgA, with p-nitrophenyl phosphate (PNPP) as the substrate. The products were quantified with an automated ELISA reader at 405 nm. For CPMV-specific titres, the results are expressed as an end-point titre, calculated as the inverse of the dilution that gave a mean $OD_{405}$ higher than the $OD_{405}$ obtained with a 1:50 dilution of pooled serum from unimmunised mice. For MUC1-specific titres, end-point titres are the inverse of the dilution that gave a mean $OD_{405}$ higher than the $OD_{405}$, obtained with a 1:50 dilution of pooled serum from wild-type CPMV-immunised mice.

Peptides. A MUC1 60-mer peptide representing 3 tandem repeats was synthesised using an automated peptide synthesizer and used for ELISA. A MUC1 16-mer peptide, corresponding to the sequence expressed on CPMV-MUC1(16) was synthesised and coupled to KLH by the EDC method (coupling efficiency approximately 15–25 peptide copies per KLH molecule).

Flow cytometry. Tumour cells (410.4, E4 and T47D; $2 \times 10^5$) were incubated with 40 µl of 1:4 diluted antisera (either NMS, or wild type-, CPMV-MUC1(16)- and CPMV-MUC1(23)-immunised serum) or 1:2 diluted monoclonal antibody HMFG2 supernatant for 1 hr on ice. After washing with PBS/3% FCS, the cells were incubated with 20 µl of 1:20 diluted PE-labelled goat anti-mouse IgG. The mean fluorescence intensity of the staining was quantified by flow cytometry (FACSCAN).

Collection of Intestinal IgA. Intestinal lavages were collected from mice as follows. Mice were culled by exsanguination and the intestines and caeca washed out with 3 ml of ice-cold 50 mM EDTA containing soybean trypsin inhibitor. The lavage fluids were centrifuged at 13000 g for 10 mins to remove large debris and then 10 µl/ml of 0.2M PMSF in ethanol (95% v/v) and 10 µl/ml of sodium azide (2% w/v) added to the clarified supernatant. Foetal calf serum was added to 3% and the samples were stored at −80° C.

EXAMPLE 1

Construction of Mucin-Displaying CVPs

The genome of CPMV consists of two molecules of single stranded plus sense RNA, (RNA1 and RNA2) which were cloned on separate plasmids as full length cDNAs (pCP1 and pCP2 respectively), as described by Dessens & Lommonossoff [*J. Gen. Virol.* (1993) 74:889–892].

Vector pCP2-0.51 is derived from pCP2 (see Example 6 of WO96/02649) and was constructed as described by Dalsgaard et al. [*Nature Biotechnology* (1997) 15:248–252]. The AatII site present in the pUC vector sequences of pCP2 was removed by linearisation of the plasmid with this enzyme, followed by treatment with the Klenow fragment of *E. coli* DNA polymerase I to eliminate the 3' overhangs, followed by re-ligation to form pCP2-AatII. PCP2-AatII was then digested with BamHI and EcoRI and the 2 kb fragment released was replaced by the equivalent fragment derived from pMT7-HRVII [Porta et al., supra]. The resultant plasmid, pCP2-0.51, therefore contained the mutated S coat protein gene containing an engineered AatII restriction site together with additional sequences coding for a fragment of the coat protein of human rhinovirus (HRV) inserted between RNA2 nucleotides 2725 and 2726.

Vector pCP2-0.51 was then digested with SacII and EcoRI to release a DNA fragment carrying the CaMV 35S promoter fused to the full-length cDNA clone of CPMV RNA2. This fragment was ligated into similarly digested pBSII SK+ (Stratagene) to make vector pCP7—HRVII. The HRV sequence together with CPMV flanking sequences were then excised by digestion with NheII and AatII and replaced by a pair of chemically synthesised overlapping oligonucleotides carrying the CPMV flanking sequences only [Usha et al., supra], thus restoring the normal CPMV sequence between these two restriction sites. All the cloning junctions described were verified by sequence analysis and the resultant vector was called pCP7. Subsequently the complete sequence of the CaMV35S-CPMV RNA2 cassette was determined between the SacII and EcoRI restriction sites.

To produce CPMV-MUC1(16) and CPMV-MUC1(23), pCP7 was digested with NheII and AatII and the excised fragment replaced by oligonucleotides coding for the excised wild-type CPMV sequences plus either a 16-mer MUC1 peptide "GVTSAPDTRPAPGSTA" (SEQ. ID No. 6) or a 23-mer MUC1 peptide "PDTRPAPGSTAPPAHGVTSAPDT" (SEQ. ID No. 7), forming plasmids pCP7-MUC1(16) and pCP7-MUC1(23), respectively.

Cowpea plants (*Vigna unguiculata* cv. Blackeye) were inoculated with linearised pCP1 and pCP7-MUC1 as described by Dessens et al. [supra]. DNA maxi-preps were made of each plasmid using the Qiagen purification system. 50 µg pCP1 were digested with MluI and 50 µg pCP7-MUC1 were digested with EcoII. The plasmids were purified by phenol/chloroform extraction and ethanol precipitation and each resuspended in 125 µl 10 mM sodium phosphate buffer pH 7.0. The plasmids were mixed together and 50 µl of the mixture were inoculated onto one primary leaf of each of five 10 day old cowpea plants by manual abrasion in the presence of carborundum powder.

All five inoculated plants developed chlorotic lesions in the inoculated leaves and a chlorotic mosaic on the secondary leaves. The recombinant virus spread throughout the growing plant in a manner similar to that of a natural infection with wild type CPMV. After 2–3 weeks, small samples (∼10 mg) of tissue were taken from the youngest leaves of each plant, which were showing good symptoms of viral infection. Each sample was ground in 400 µl 0.1M sodium phosphate buffer, the extract was emulsified with an equal volume of a 1:1 mixture of chloroform/n-butanol, clarified by centrifugation and the aqueous phase was retained. 100 µl of 1 M NaCl/20% PEG 8000 were added, followed by incubation on ice for 20 minutes. The precipitate was collected by centrifugation for 5 min and resuspended in 20 µl sterile deionised water. 2 µl of each particle 'mini-prep' were then analysed by RT-PCR and agarose gel electrophoresis, and the products of the PCR reaction were sequenced. In all 5 plants, a single band of the expected size was seen in the RT-PCR reaction and the sequence data showed that the sequence of the inserted RNA was correct in each case.

The leaf material of all the plants was then harvested and the recombinant virus purified according to standard techniques (as described in Example 2 of WO96/02649) and the final product sterilised by filtration through a 0.2 µm membrane. 5 µg of the purified virus were analysed by SDS-PAGE followed by staining with coomassie brilliant blue. A band corresponding to the virus L subunit was seen together with a band characteristic of the S coat protein containing an inserted peptide. The purified particles were also analysed via RT-PCR, and the PCR products further characterised by sequencing. The sequence of the inserted RNA was found to be correct.

The characterised particles from the first round of infection were designated as master stocks and used to initiate a second round of infection in a further five plants in order to generate a working stock [as described by Usha et al., supra]. After 2–3 weeks the plant leaves were harvested and the recombinant virus purified and characterised as before, with the same results. This demonstrated that the inserted peptide sequence was stable over at least two passages.

Each CVP expressed 60 copies of the appropriate MUC1 peptide sequence. 1 µg CVP contains approximately 17 ng of the appropriate peptide sequence.

EXAMPLE 2

Immunogenicity of MUC1-based CVPs

Mice (8 per group) were immunised subcutaneously with 100 μg of CPMV-MUC1 (16), CPMV-MUC1( 23) or wild-type CPMV in Freund's complete adjuvant (FCA). Subsequent 25 μg boosters in incomplete Freund's adjuvant (IFA) were administered on day 14 and 28, and sera collected on day 42 for analysis by ELISA.

Both engineered CVPs and the wild-type CPMV elicited very high titres of CPMV-specific antibody on day 42 (FIGS. 2A–C). However, only the CVP-immunised mice produced MUC1-specific antibody, which was not detected in the sera of wild type immunised mice (FIGS. 2A–C). Titres elicited by CPMV-MUC1(16) (mean titre of 100,800) and CPMV-MUC1(23) (mean titre of 86,300) were generally similar.

Thus CPMV is a highly effective carrier of peptides from the MUC1 tandem repeat for vaccination purposes. The three doses of CVP which were administered totalled 150 μg, which constitutes only ~3 μg MUC1 peptide.

EXAMPLE 3

CVP-Immunised Mouse Sera Stain MUC1-Expressing Tumour Cell Lines

Sera from mice immunised with the above CVPs in FCA were shown to stain mouse E4 and human T47D tumour cells, both of which express MUC1, very intensely by flow cytometric analysis (FIG. 3A). The staining of both cell lines using sera from CPMV-MUC1(16)-immunised mice was stronger than that of CPMV-MUC1(23)-immunised sera (FIG. 3A). The staining of T47D cells using sera from CPMV-MUC1(16)-immunised mice was comparable to that achieved with the anti-MUC1 mAb HMFG2.

In a second experiment, sera from mice immunised with CPMV-MUC1(16) in QS-21 also strongly stained the two MUC1-expressing cell lines but not the MUC1-negative 410.4 cells (FIG. 3B). In both studies, the staining was highly specific since the staining of the MUC1-expressing cells with sera from wild-type CPMV-immunised mice and normal mouse serum was extremely weak. Mice immunised with the MUC1 peptide conjugated to KLH elicited only low titres of MUC1-specific IgG and consequently stained the cells only very weakly (FIG. 3B).

The intense specific staining of the cells could also be visualised under a fluorescence microscope. Sera from CPMV-MUC1(16)-immunised mice strongly stained both cell lines, which were only very weakly stained with sera from wild-type CPMV-immunised mice. In contrast, the staining of MUC1-negative 410.4 cells was extremely weak.

Sera from CPMV-MUC1(16) and CPMV-MUC1(23)-immunised mice was also demonstrated to specifically stain fresh human breast cancer tissue (data not shown).

Serum obtained following intranasal immunisation with MUC1(16)+QS-21 was also able to stain T47D cells (data not shown).

EXAMPLE 4

CPMV is a more Effective Carrier of MUC1 Peptide than KLH

Mice were immunised subcutaneously on days 0 and 21 with 10 μg CPMV-MUC1(16) or 10 μg MUC1-KLH, using QS-21 adjuvant in both cases. The generation of MUC1-specific antibody was very rapid as levels were detectable on day 14 (not shown) and had reached high levels 21 days after primary immunisation (FIG. 4). KLH was a far less effective carrier than CVPs for generating MUC1-specific IgG even when adjuvant was used.

Immunisation with 100 μg CPMV-MUC1(16), with and without QS-21 adjuvant, also gave food antibody responses (FIG. 4). Presenting two 2 μg doses of peptide, as contained in 100 μg of the CVP, without additional adjuvant thus leads to high levels of serum antibody which exceed those attained using two 100 μg doses of the MUC1 peptide conjugated to KLH using QS-21 as adjuvant. Thus, the CVP presented 50-fold less peptide than the peptide-KLH conjugate and still induced a 50-fold increase in the titre of anti-peptide antibody in the immunised animals.

In a further set of experiments, mice (5 per group) were immunised subcutaneously on days 0 and 14 with 1 μg or 10 μg CPMV-MUC1(16) or with 50 μg MUC1-KLH. QS-21 was used as an adjuvant in all immunisations. The end-point antibody titres on day 21 were as follows:

| Immunogen | Mouse No. | | | | |
|---|---|---|---|---|---|
| | 1 | 2 | 3 | 4 | 5 |
| 10 μg CPMV-MUC1 (16) | 6400 | 12800 | 51200 | 51200 | 208400 |
| 1 μg CPMV-MUC1 (16) | 25600 | 25600 | 25600 | 25600 | 102400 |
| 50 μg MUC1-KLH | 3200 | 3200 | 102400 | 3200 | 150 |

The conclusion is that two doses of 1 μg CPMV-MUC1 (16) (~20 ng of 16-mer peptide per dose) induced generally higher and more consistent titres of anti-peptide antibodies than did two doses of 50 μg of the MUC1 16mer peptide conjugated to KLH. This is particularly remarkable since there is in excess of 2000-fold more peptide being presented by the KLH conjugate. Similarly high post-immunisation (day 28) titres were seen in mice immunised with either 0.5 μg or 5 μg CPMV-MUC1(16) on days 0 and 21. The 0.5 μg dose gave a titre comparable to the previous 50 μg KLH-MUC1 experiment.

EXAMPLE 5

CPMV is a more effective MUC1 carrier than KLH in MUC1-transgenic mice

To be effective in humans, a MUC1-based vaccine must be able to overcome immune privilege and elicit MUC1-specific antibodies when present as a self antigen. In the previous examples, the MUC1 peptides were not functioning as self antigens, but were foreign (mouse and human sequences ~30% homology). To address this issue, mice transgenic for human MUC1 were tested [Graham, et al. (1996) Int. J. Cancer 65:664–670] as a better model of humans.

Transgenic mice expressing human MUC1 and non-transgenic mice were immunised subcutaneously with 100 μg of CPMV-MUC1(16), wild type CPMV or 25 μg MUC1-KLH, using QuilA adjuvant, and boosted with the same dose on day 14. Sera were pooled for mice in the same group, except for the transgenic mice immunised with CPMV-MUC1(16) which were analysed individually (FIG. 5).

Figure 5:
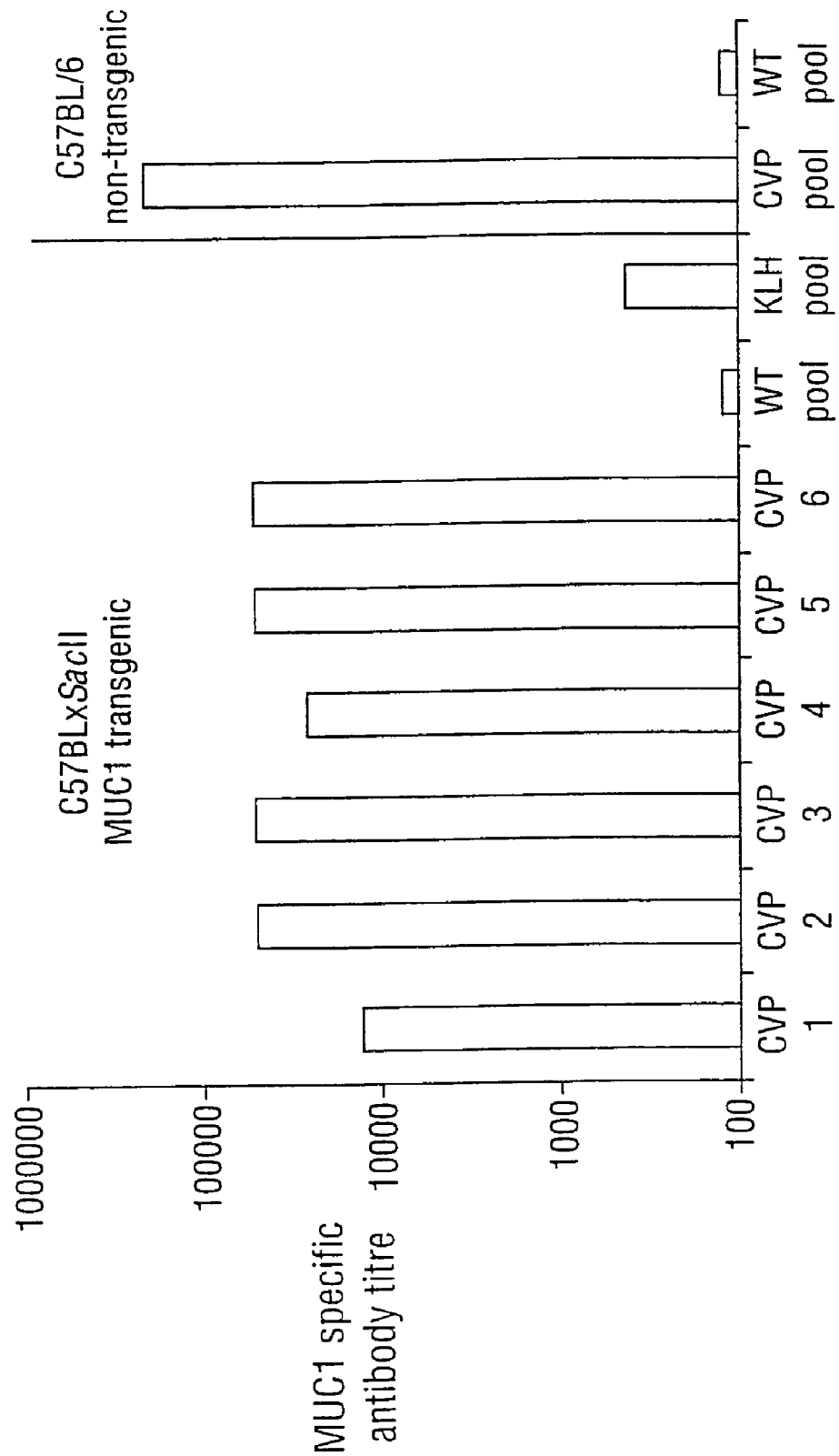
FIG. 5 shows antibody titres induced in six transgenic mice using CVPs of the invention (CVP 1 to 6). Control samples were pooled.

CPMV-MUC1(16) was shown to be highly immunogenic in human MUC1-transgenic mice with anti-MUC1 peptide antibody titres only a little lower than those elicited in non-transgenic mice (FIG. 5). Moreover, the anti-MUC1 peptide antibodies elicited in the transgenic mice by CPMV-MUC1(16) immunisation were considerably greater than those elicited by the MUC1 peptide conjugated to KLH (FIG. 5). The average titres of anti-MUC1 antibodies were 40,500 following immunisation with CPMV-MUC1(16), 400 following immunisation with MUC1-KLH, and 120 following immunisation with wild type CPMV (see FIG. 5). These data confirm and further support the enhanced presentation system of the present invention by demonstrating that the presentation of a mucin peptide on the surface of a plant virus is significantly better than the presentation as conjugated to KLH (the conventional carrier).

In summary, over 10-fold less peptide was presented on CPMV as compared to KLH, and a 100-fold higher level of anti-peptide antibody was induced by CPMV-MUC1(16) as compared to corresponding presentation by KLH (1,000-fold difference in total).

EXAMPLE 6

Relative Efficacy of Adjuvants to Augment CPMV-MUC1(16) Responses

Because FCA is not a suitable adjuvant for human use, further studies were conducted with CPMV-MUC1(16) adjuvanted with less toxic adjuvants including the saponin-based adjuvants QuilA (20 µg/dose), QS-21 (20 µg/dose) and ISCOM matrix (10 µg/dose), or with algammulin (a mixture of alum and gamma-inulin: 10 µg/dose). Mice were immunised subcutaneously with 50 µg CPMV-MUC1(16) in the above adjuvants and boosted with 25 µg on days 14 and 28 with the same adjuvant.

Figure 6:
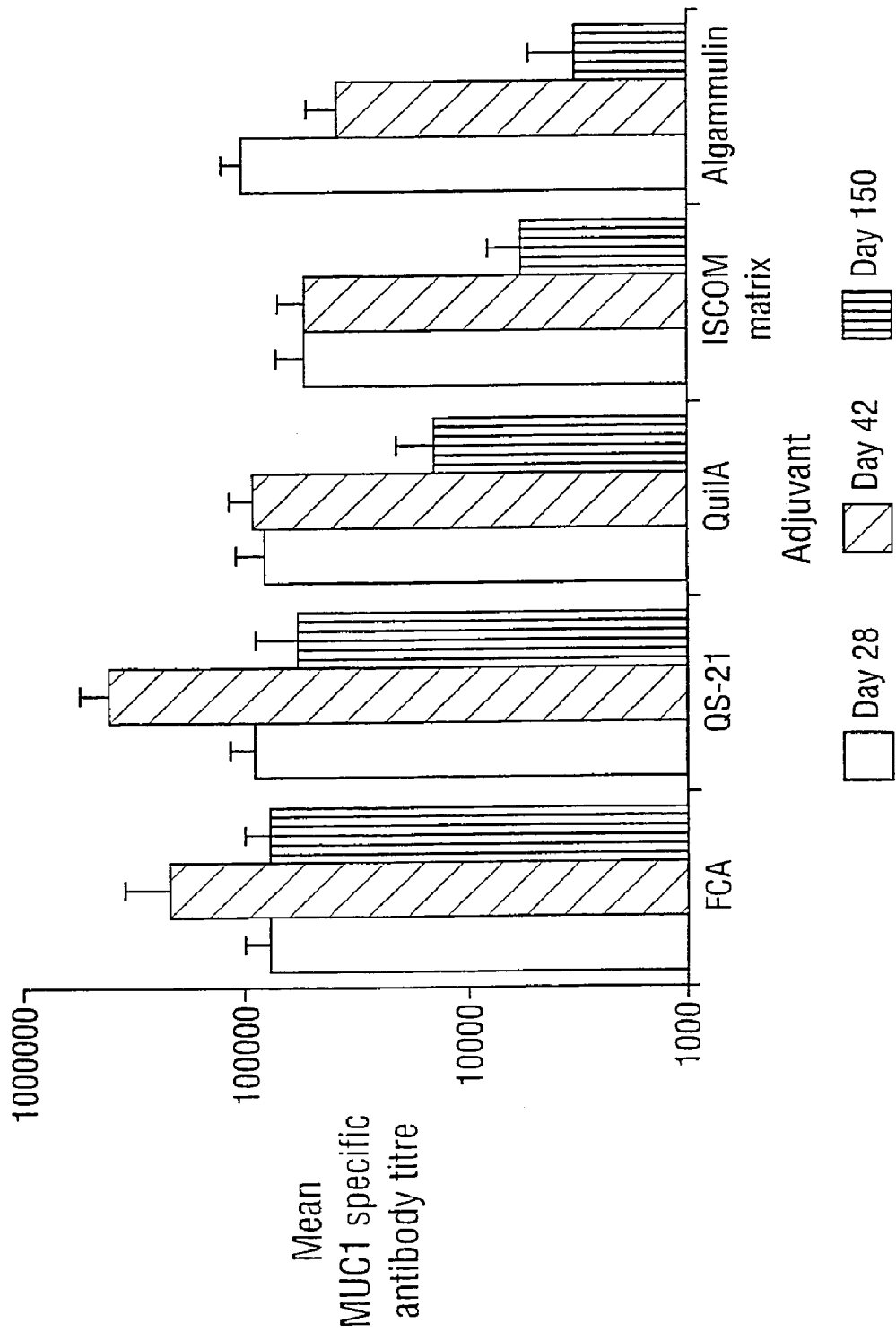
FIG. 6 shows the effect of various adjuvants on IgG1/IgG2a titres. Titres are expressed as the mean end-point titre obtained with the sera from individual mice within each group. Standard deviations are shown for each value.

Mice immunised with CPMV-MUC1(16) in QS-21 elicited higher titres of MUC1-specific antibody than all other adjuvants tested (FIG. 6), including FCA, when assayed on day 42. Titres in all the adjuvant groups remained high for 70 days and then began to drop, except for the FCA and QS-21 groups which still had high titres on day 150 (mean titres of 76,800 and 57.600 respectively; FIG. 6).

Thus QS-21 facilitates optimal and sustained responses to CVPs and, together with its favourable safety profile, provides a suitable choice as an adjuvant for inclusion in a CVP-based cancer vaccine for human use.

EXAMPLE 7

Exogenous Adjuvant is not Required for CVPs of the Present Invention

Mice were immunised subcutaneously with 100 µg of CPMV-MUC1(16) on days 0 and 21 with QS-21 and on days 0 and 14 without QS-21 as adjuvant. On day 35, the titres of the anti-MUC1 peptide antibodies were not very different between the mice immunised with or without adjuvant (see FIG. 4). Although the use of QS-21 is beneficial in increasing, and probably also prolonging, the immune response to the mucin peptide present on the CPMV particle, the use of an adjuvant such as QS-21 is not essential. CPMV-MUC1 (16) administered without any adjuvant induced a good immune response to the MUC1 peptide.

EXAMPLE 8

Intranasal Vaccination

Mice were immunised intranasally on days 0, 7, 14, and 21 with 100 µg per dose of CPMV-MUC1( 16) or wild-type CPMV. The immunisations were performed with or without the use of cholera toxin (CT). CT has nasal adjuvant activity via its ability to recognise certain cell-surface receptors and thus aid in the delivery of antigen to professional antigen presenting cells.

The titres of anti-peptide IgG antibodies in the sera following intranasal administration of CPMV-MUC1(16) were approximately the same when the CVP was administered with or without CT (1:53,440 with CT, 1:57,680 without CT, see FIG. 7A). In addition, high titres of anti-MUC1 IgA antibodies in intestinal lavages were found in animals immunised with or without CT (see FIG. 7B).

The conclusion is that CT is not necessary to induce mucosal or systemic immune responses to CPMV-MUC1 (16) administered via a nasal route. Furthermore. CT does not enhance the immune response to CPMV-MUC1 (16) following intranasal administration.

In further experiments, ISCOMs were used as intranasal adjuvants in place of CT. Mice were immunised with 4 doses of 100 µg CPMV-MUC1(16)+10 µg ISCOM matrix. On days 42, high titres of CPMV- and MUC1-specific IgG were detected in sera, and specific IgA in bronchial, intestinal and, to a lesser extent, vaginal lavages (FIG. 7C). The titres obtained with ISCOMs, however, were not significantly higher than those obtained without any exogenous adjuvant.

EXAMPLE 9

Th1 Bias

In mice, Th1 cells mediate macrophage and cytotoxic T cell activation and B cell class-switching to the $IgG_{2a}$ sub-class [Mosmann et al. (1986) J. Immunol. 136:2248–2357]. $IgG_{2a}$ is the principal effector isotype of IgG that induces antibody-dependent cell cytotoxicity (ADCC) and phagocytosis, and better protects mice against tumours [Kaminksi et al. (1986) J. Immunol. 136:1123–1130]. Conversely, Th2 cells induce B cells to produce $IgG_1$, which is ineffective at mediating ADCC or phagocytosis. In view of the opposing functions of Th1 and Th2 CD4+ cells and of the IgG isotypes generated by these subsets, it is desirable for cancer vaccines to prime Th1 cells.

The isotype of MUC1-specific antibodies was examined in mice immunised with two doses of 100 µg CPMV-MUC1 (16) without adjuvant, or two doses of 10 µg or 100 µg CPMV-MUC1(16) in QS-21. Titres of all isotypes were present, but $IgG_{2a}$ and $IgG_{2b}$ were predominant over $IgG_1$. This bias towards a Th1-type response was most pronounced in the absence of adjuvant. The control mice, immunised with KLH-MUC1 in QS-21, produced predominantly $IgG_1$.

The bias of the isotype response appear to be related to the ability of the virus to prime virus-specific Th1 cells which produce IFN-γ but little IL-4, allowing class-switching of peptide-specific B cells to $IgG_{2a}$-producing plasma cells.

EXAMPLE 10

Vaccination with CPMV-MUC1(16) Causes a Reduction in Tumour Burden

The ability of CPMV-MUC1(16) to elicit antibodies which can cause regression of tumours expressing the MUC1 protein was demonstrated in a mouse tumour model. Tumour cells expressing the MUC1 protein were injected subcutaneously into mice which had previously been immunised with CPMV-MUC1(16). Full details are described below.

Nine C57BLScSn mice were immunised subcutaneously with 100 µg of CPMV-MUC1(16) on day 0 and 21 using Quil A (10 mg/dose) as adjuvant. A further 6 mice were immunised with phosphate buffered saline containing QuilA (PBSA) in a similar manner. On day 42 all mice were administered with $2\times10^5$ MUC1 RMA cells by subcutaneous injection in the flank and the tumour size measured in two dimensions over the following month using vernier calipers. Tumour volumes were calculated as $(a\times b^2)/2$ where a represents the largest diameter and b the smallest diameter. Mice were sacrificed when tumours reached −1 to 1.5 cm in diameter. The results are summarised below:

| Vaccine | Mouse No. | Days post challenge |  |  |  |  |  |  |
|---|---|---|---|---|---|---|---|---|
|  |  | 9 | 14 | 16 | 21 | 23 | 28 | 30 |
| CVP | 1 | 0.108 | 0.06 | 0 | 0 | 0 | 0 | 0 |
|  | 2 | 0.0108 | 0.06 | 0.032 | 0.032 | 0.032 | 0.013 | 0.004 |
|  | 3 | 0.05 | 0.05 | 0 | 0 | 0 | 0 | 0 |
|  | 4 | 0.062 | 0.032 | 0 | 0 | 0 | 0 | 0 |
|  | 5 | 0.062 | 0.062 | 0.062 | 0.0864 | 1.14 | 1.8 |  |
|  | 6 | 0.108 | 0.126 | 0.196 | 0.6 | 0.85 | 1.617 |  |
|  | 7 | 0.126 | 0.126 | 0.441 | 0.441 | 0.793 | 1.68 |  |
|  | 8 | 0.126 | 0.126 | 0.108 | 0 | 0 | 0 |  |
|  | 9 | 0.075 | 0.148 | 0.22 | 1.27 |  |  |  |
| PBSA | 10 | 0.126 | 0.5 | 0.55 | 1.68 |  |  |  |
|  | 11 | 0.108 | 0.428 | 0.5 | 1.37 |  |  |  |
|  | 12 | 0.17 | 0.256 | 0.936 |  |  |  |  |
|  | 13 | 0.075 | 0.5 | 0.55 | 1.37 |  |  |  |
|  | 14 | 0.0907 | 0.108 | 0.108 | 0.256 | 0.5 | 1.372 |  |
|  | 15 | 0.171 | 0.5 | 0.726 | 1.47 |  |  |  |

It can be seen from the above data that over 50% of the mice (5/9 mice) immunised with CPMV-MUC1 were protected compared to 0% (6/6) in the PBSA-immunised control group.

EXAMPLE 11

Further Insertion Points in VP-S of CPMV

Examples 1–10 illustrate the presentation of a tumour-associated mucin at the βB–βC insertion site of the CPMV S subunit. Alternative insertion sites within the S subunit are also suitable for achieving the CVPs of the present invention. In this respect, knowing the nucleic acid sequence encoding the S subunit and a range of desired insertion locations therein, the skilled person can simply prepare a suitable expression vector in a manner analogous to the preparation of pCP7. Similarly, knowing the nucleic acid sequence encoding the L subunit of CPMV and a range of desired insertion locations therein, the skilled person can simply prepare an expression vector encoding, inter alia, the L subunit in a manner analogous to the preparation of pCP7.

Although examples 1 to 10 employ the MUC1(16) and MUC1(23) epitopes, any mucin peptide epitope sequence can be used.

As mentioned above, a mucin peptide (e.g. the 16-mer) can be inserted in the βC'βC" loop of the small coat protein of CPMV. For example, the peptide can be cloned in between $D_{44}+D_{45}$, in a suitable vector. This results in a good viral yield with good immunological properties.

Insertions in the βC'βC"loop can also be combined with insertions in the C-terminus of the VP-S. The C-terminus of VP-S sticks out from the surface of the virion and is highly immunogenic. The region that is not part of the "body" of the virus starts with $Pro_{182}$ and runs up to the C-terminus $Ala_{213}$. Insertions of mucin epitopes can be made in this region, with a particularly effective insertion site being between $R_{199}$ and $S_{200}$.

EXAMPLE 12

Insertions in SBMV

The following examples illustrate the application of the present invention to plant viruses other than CPMV—any icosahedral plant virus can be used as a potential carrier for these mucin peptides. This example describes the use of SBMV instead of CPMV as a carrier for the MUC1 (16) epitope.

Inspection of the crystal structure of SBMV strain C reveals that a portion of the loop between the βH and βI strands is well exposed upon the surface of the virus at the five-fold and quasi-six fold axes. This portion of the loop comprises amino-acids 251 to 255 of the linear coat protein sequence and nucleotides 3967 to 3981 of the genomic RNA sequence.

The cDNA of the complete 4194 bp RNA genome of SBMV is cloned into a derivative of pBluescriptII plasmid vector lacking the T7 and T3 promoters using standard techniques. The cDNA is cloned immediately downstream of a bacteriophage T7 such that a unique restriction enzyme site is present at the 3' terminus of the cDNA, thus allowing linearisation of the recombinant plasmid to generate run-off transcripts which mimic the wild-type RNA. As an alternative, the cauliflower mosaic virus (CaMV)35S promoter may be used.

A sub-clone is then made from this full-length cDNA clone by inserting the BgII-XmnI fragment (genomic RNA nucleotides 3165–4161), which contains within it the whole coat protein open reading frame, into BamHI/HincII digested pBluescriptII. This sub-clone is further manipulated via site-directed mutagenesis at genomic nucleotide positions 3969 (change A to C) and 3984 (G to T) to create BamHI and HpaI restriction sites, respectively (FIG. 8A). The modified subclone is digested with these enzymes and separated from the small excised fragment which is replaced by oligonucleotides coding for the excised nucleotide sequence plus nucleotides coding for the MUC1(16) insert. The five constructs shown in FIG. 8B contain the insert between coat protein amino acids 251–252, 252–253, 253–254, 254–255, or 255–256.

The modified region of the coat protein from each of these constructs is isolated on a HindIII/AvrII fragment (genomic nucleotides 3434–4096) and used to replace the corresponding fragment in the full-length cDNA clone of the virus. Each of these clones is then linearised at the 3' terminus of the cDNA and, in the case of a T7 bacteriophage promoter construct, used to generate capped run-off RNA transcripts which are then inoculated onto the host-plant (*Vigna unguiculata*), or inoculated directly when under the control of the 35S promoter.

The inoculated plants are monitored for symptoms, and the strength of symptoms, yield and stability for each construct are assessed in order to determine the optimal insertion site. If desirable, purified virus may also be used to immunise experimental animals in order to determine the levels of immune response generated by each construct.

This example can be extrapolated to allow insertion in any of the exposed loops of SBMV. Similarly, any mucin peptide epitope sequence can be used instead of MUC1(16).

EXAMPLE 13

Insertions in LTSV

This example describes the determination of a potential insertion site for epitopes by alignment of the primary sequence of a virus whose structure is unknown (LTSV), against those of viruses whose structure has been determined.

The crystal structures of two sobemoviruses (SBMV and SMV) have been solved at high resolution. Comparison of the crystal structures reveals that secondary structural elements are well conserved between the viruses and, in particular, the protruding loop between the βH and βI is almost identical in shape and location between the two viruses. This structural element would therefore be expected to be well conserved in all sobemoviruses.

Alignment of the primary sequences of LTSV, SBMV and SMV shows a strong conservation of residues between the three viruses within the βH strand region and significant sequence homology within the βI strand (FIG. 9). This allows the loop region of LTSV to be inferred as spanning amino acids 218 to 224 of the coat protein.

The 4275 bp LTSV RNA genome is cloned as cDNA, as described for SBMV in example 12. The genomic clone is then modified by site directed mutagenesis at position 3959 (C to T) and position 3998 (T to C) to create unique PstI and KpnI restriction enzyme sites, respectively (FIG.10A). The modified genomic clone is digested with these restriction enzymes and separated from the small excised fragment which is replaced by oligonucleotides coding for the excised nucleotide sequence plus nucleotides coding for the epitope sequence MUC1(16). The six constructs shown in FIG. 10B contain the epitope sequence between coat protein amino acids 218–219, 219–220, 220–221, 221–222, 222–223, or 223–224.

Each of these clones is linearised at the 3' terminus of the cDNA and, in the case of a T7 bacteriophage promoter construct, used to generate capped run-off RNA transcripts which are then inoculated onto the host-plant (*Nicotiana clevelandii*), or inoculated directly when under the control of the 35S promoter. The inoculated plants are used as described in example 12.

This example can be adapted to insert of any peptide into any of the exposed loops of LTSV.

EXAMPLE 14

Insertions in RCNMV

Like example 13, this example describes the determination of potential insertion sites in a virus (red clover necrotic mosaic virus, RCNMV), whose crystal structure is unknown, using primary structural alignments with a second virus whose crystal structure has been determined (TBSV). This example uses secondary structure prediction algorithms.

The crystal structure of the coat protein of TBSV reveals that each of the 180 coat protein subunits forming the T=3 icosahedron consists of two β-barrel domains. The first domain forms the surface of the virus particle and is termed the S domain and is equivalent to the single domain found in SBMV. The second, much smaller, domain forms a surface protrusion at right angles to the plane of the S domain. This P domain forms dimeric interactions with the P domain of a neighbouring coat-protein subunit at the strict and quasi two-fold axes of the icosahedron. The presence of the P domain causes the virions to appear distinctly granular when examined under the electron microscope. Between the S and P domains is a short flexible linker followed by a pair of β-strands connected by a loop which appears to be highly exposed on the viral surface with no obvious role in the contacts between subunits. This loop provides a potential target for epitope insertions.

Dianthoviruses (e.g. RCNMV) also appear distinctly granular when subjected to electron microscopy, and this together with the size of the coat proteins and their limited homology with those of tombusviruses suggests that they may have structural similarity. Alignment of the coat protein sequences of RCNMV and TBSV (FIG.11) using a Lipman-Pearson alignment algorithm, which recognises sequence conservation as well as identity, gives a similarity index of 26.9 (strict homology is 23%). From the alignment it can be seen that the S domain is better conserved (TBSV residues 100 to 269, strict homology 36%) than the P domain (TBSV residues 270–388, poorly conserved).

Figure 12:
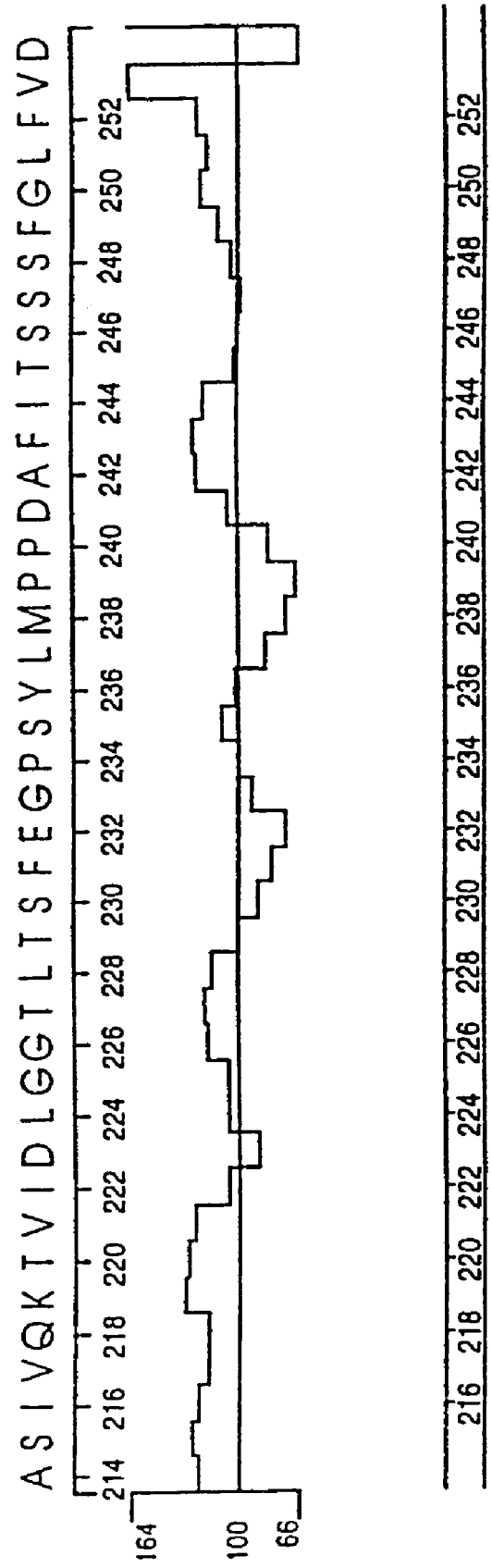
FIG. 12 shows a Chou-Fasman β-region prediction plot for RCNMV coat protein residues 214–254 (SEQ ID NO:29), using an algorithm based upon the structures found in 64 proteins.

The loop of interest comprises TBSV residues $L^{280}A^{281}G^{282}$ and the sequence around this region shows some similarity to the sequence of RCNMV. Secondary structure prediction algorithms are also used to predict the location of β-strands, however, and hence the loops which lie between them. FIG. 12 shows a Chou-Fasman β-region prediction plot of RCNMV residues 214–254 using an algorithm based upon the structures found in 64 proteins which is claimed to be 80% accurate at predicting β-strands of interest. The plot suggests that β-strands of interest are located between residues 214–221 and 226–228, and hence the loop at the tip of the domain will be residues 222–225 and residues 245–248. A more sophisticated prediction algorithm, the EMBL PHDsec program based upon trained neural networks, may also be used. The resulting output for the region of interest is shown in FIG. 13. This locates the β-strands to residues 220–223 and 227–239, therefore the loop is comprised of residues 224–226. Combining the two sets of data, the loop will lie within the region spanned by residues 222 to 226.

Dianthoviruses have a bipartite RNA genome, both RNAs being required for infectivity. Accordingly, RCNMV RNAs 1 and 2 are cloned as cDNA, using standard molecular biological techniques, into a suitable vector, downstream of a CaMV 35S promoter. As an alternative, the T7 promoter may be used. Both clones are engineered such that they can be linearised at the 3' termini of the cDNAs.

The cDNA genomic clone of RNA1 is modified by site directed mutagenesis at positions 3078 (A to G) and 3081 (G to C), to create a unique ApaLI restriction site, and at positions 3108 to 3111 (ACTC to GTTA) to create a unique HpaI restriction site (FIG. 14A). Although the mutation at position 3081 is not silent, the correct codon can be restored when ligating in oligonucleotides to generate the epitope insertion. The modified genomic clone is digested with these restriction enzymes and separated from the small excised fragment which is replaced by oligonucleotides coding for the excised nucleotide sequence plus nucleotides coding for the MUC1(16) epitope. The six constructs shown in FIG. 14B insert the epitope sequence between coat protein amino acids 221–222, 222–223, 223–224, 224–225, 225–226, or 226–227.

As in examples 12 and 13, each of these clones is linearised at the 3' terminus of the cDNA and, in the case of a T7 promoter construct, used to generate capped run-off RNA transcripts. These are then mixed with similar transcripts from the linearised cDNA clone of genomic RNA2 and inoculated onto the host-plant. Linearised clones are inoculated directly when under the control of the CaMV 35S promoter. Inoculated plants are used as described previously.

This example can be adapted to allow insertions of any peptide into any exposed RCNMV loop.

It will be understood that the invention has been described by way of example only and modifications may be made whilst remaining within the scope and spirit of the invention.

What is claimed is:

1. A chimaeric virus particle derived from a plant virus having a coat protein with a beta barrel structure and modified by insertion of a peptide epitope of a tumour associated mucin at an exposed region in the coat protein in a loop connecting beta sheets.

2. A chimaeric virus particle according to claim 1, in which the tumour associated mucin is PEM.

3. A chimaeric virus particle according to claim 2, in which the insert is a peptide comprising at least five amino acids of the 20 amino acid repeat set forth in SEQ ID NO:1, of the extracellular portion of the MUC1 transmembrane molecule.

4. A chimaeric virus particle according to claim 3, in which the peptide is a 16-mer set forth as SEQ ID NO:6.

5. A chimaeric virus particle according to claim 1, in which the plant virus is a comovirus.

6. A chimaeric virus particle according to claim 5, in which the plant virus is cowpea mosaic virus.

7. A chimaeric virus particle according to claim 6, in which the insert is present in the S protein of the virus.

8. A method for producing a chimaeric virus particle according to claim 1, which comprises introducing a nucleotide sequence coding for the peptide epitope of a tumour-associated mucin into the plant viral nucleic acid which codes for the coat protein, such that said peptide epitope is inserted in an exposed region in the coat protein in a loop connecting beta sheets; infecting plants, plant tissue, plant cells, or protoplasts with the modified viral nucleic acid; and harvesting chimaeric virus particles.

9. A method according to claim 8, applied to an RNA plant virus, which comprises introducing a DNA coding for the peptide epitope into a cDNA corresponding to the RNA of the plant virus which codes for an exposed portion of its coat protein; inoculating plants, plant tissue, plant cells, or protoplasts with the thus modified cDNA or an RNA transcript thereof, if necessary together with any other DNA or RNA required for multiplication and assembly of whole virus particles in the plant material; and harvesting chimaeric virus particles.

10. A method according to claim 9, in which the modified cDNA is produced by introducing the DNA encoding the peptide epitope into a DNA fragment excised from the plant viral cDNA, and reinserting the modified excised fragment so as to constitute the plant viral cDNA in modified form.

11. A method according to claim 8, in which modified virus produced, or RNA extracted therefrom, is passaged in plants to produce further yields of modified virus.

12. A composition comprising chimaeric virus particles according to claim 1 as an immunogenic component thereof.

13. A composition according to claim 12, further comprising an adjuvant.

14. A composition according to claim 13, in which the adjuvant is selected from Freund's complete adjuvant, QuilA, QS-21, ISCOM matrix, alum, algammulin; or combinations thereof.

15. A composition according to claim 12, said composition being free from exogenous adjuvant.

16. A chimaeric virus particle according to claim 3, in which the peptide is a 23-mer peptide set forth as SEQ ID NO:7.

17. A chimaeric virus particle according to claim 3, in which the peptide comprises the amino acid sequence set forth as SEQ ID NO:2.

18. A chimaeric virus particle according to claim 3, in which the peptide comprises the amino acid sequence set forth as SEQ ID NO:3.

* * * * *

SEQUENCE LISTING

<160> NUMBER OF SEQ ID NOS: 38

<210> SEQ ID NO 1
<211> LENGTH: 20
<212> TYPE: PRT
<213> ORGANISM: Artificial Sequence
<220> FEATURE:
<223> OTHER INFORMATION: Synthetic

<400> SEQUENCE: 1

Pro Asp Thr Arg Pro Ala Pro Gly Ser Thr Ala Pro Pro Ala His Gly
 1               5                  10                  15

Val Thr Ser Ala
            20

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Pro Asp Thr Arg Pro
 1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Ala Pro Asp Thr Arg
 1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Asp Ala His Trp Glu Ser Trp Leu
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Asp Leu His Trp Ala Ser Trp Val
 1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic -continued

```
<400> SEQUENCE: 6

Gly Val Thr Ser Ala Pro Asp Thr Arg Pro Ala Pro Gly Ser Thr Ala
1               5                   10                  15

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Pro Asp Thr Arg Pro Ala Pro Gly Ser Thr Ala Pro Pro Ala His Gly
1               5                   10                  15

Val Thr Ser Ala Pro Asp Thr
            20

<210> SEQ ID NO 8
<211> LENGTH: 39
<212> TYPE: DNA
<213> ORGANISM: Soybean mosaic virus

<400> SEQUENCE: 8
atggaaggag gatcatctaa gactgctgtg aacactggg                          39

<210> SEQ ID NO 9
<211> LENGTH: 13
<212> TYPE: PRT
<213> ORGANISM: Soybean mosaic virus

<400> SEQUENCE: 9

Met Glu Gly Gly Ser Ser Lys Thr Ala Val Asn Thr Gly
1               5                   10

<210> SEQ ID NO 10
<211> LENGTH: 48
<212> TYPE: DNA
<213> ORGANISM: Soybean mosaic virus

<400> SEQUENCE: 10
ggtgttactt ctgctcctga tactagacct gctcctggtt ctactgct                48

<210> SEQ ID NO 11
<211> LENGTH: 68
<212> TYPE: DNA
<213> ORGANISM: Artificial Sequence
<220> FEATURE:
<223> OTHER INFORMATION: Synthetic

<400> SEQUENCE: 11
gatccggtgt tacttctgct cctgatacta gacctgctcc tggttctact gcttctaaga   60
ctgctgtt                                                            68

<210> SEQ ID NO 12
<211> LENGTH: 68
<212> TYPE: DNA
<213> ORGANISM: Artificial Sequence
<220> FEATURE:
<223> OTHER INFORMATION: Synthetic

<400> SEQUENCE: 12
gatcctctgg tgttacttct gctcctgata ctagacctgc tcctggttct actgctaaga   60
ctgctgtt                                                            68
```

<210> SEQ ID NO 13
<211> LENGTH: 68
<212> TYPE: DNA
<213> ORGANISM: Artificial Sequence
<220> FEATURE:
<223> OTHER INFORMATION: Synthetic

<400> SEQUENCE: 13
gatcctctaa gggtgttact tctgctcctg atactagacc tgctcctggt tctactgcta      60
ctgctgtt                                                                68

<210> SEQ ID NO 14
<211> LENGTH: 68
<212> TYPE: DNA
<213> ORGANISM: Artificial Sequence
<220> FEATURE:
<223> OTHER INFORMATION: Synthetic

<400> SEQUENCE: 14
gatcctctaa gactggtgtt acttctgctc ctgatactag acctgctcct ggttctactg      60
ctgctgtt                                                                68

<210> SEQ ID NO 15
<211> LENGTH: 68
<212> TYPE: DNA
<213> ORGANISM: Artificial Sequence
<220> FEATURE:
<223> OTHER INFORMATION: Synthetic

<400> SEQUENCE: 15
gatcctctaa gactgctggt gttacttctg ctcctgatac tagacctgct cctggttcta      60
ctgctgtt                                                                68

<210> SEQ ID NO 16
<211> LENGTH: 33
<212> TYPE: PRT
<213> ORGANISM: Lucerne transient streak virus

<400> SEQUENCE: 16

Asn Ile Tyr Ala Pro Ala Arg Leu Thr Ile Ala Ala Ala Asn Ser Ser
1               5                   10                  15

Ile Asn Ile Ala Ser Val Gly Thr Leu Tyr Ala Thr Tyr Glu Val Glu
            20                  25                  30

Leu

<210> SEQ ID NO 17
<211> LENGTH: 37
<212> TYPE: PRT
<213> ORGANISM: Soybean mosaic virus

<400> SEQUENCE: 17

Asn Ile Gly Asn Ile Leu Val Pro Ala Arg Leu Val Ile Ala Met Glu
1               5                   10                  15

Gly Gly Ser Ser Lys Thr Ala Val Asn Thr Gly Arg Leu Tyr Ala Ser
            20                  25                  30

Tyr Thr Ile Arg Leu
        35

<210> SEQ ID NO 18
<211> LENGTH: 37
<212> TYPE: PRT
<213> ORGANISM: Soybean mosaic virus -continued

<400> SEQUENCE: 18

```
Asn Ile Ala Thr Asp Leu Val Pro Ala Arg Leu Val Ile Ala Leu Leu
1               5                   10                  15

Asp Gly Ser Ser Ser Thr Ala Val Ala Ala Gly Arg Ile Tyr Ala Ser
            20                  25                  30

Tyr Thr Ile Gln Met
        35
```

<210> SEQ ID NO 19
<211> LENGTH: 51
<212> TYPE: DNA
<213> ORGANISM: Lucerne transient streak virus

<400> SEQUENCE: 19

```
atagccgcag ctaacagctc cataaacata gctagtgtgg gtactcttta t             51
```

<210> SEQ ID NO 20
<211> LENGTH: 17
<212> TYPE: PRT
<213> ORGANISM: Lucerne transient streak virus

<400> SEQUENCE: 20

```
Ile Ala Ala Ala Asn Ser Ser Ile Asn Ile Ala Ser Val Gly Thr Leu
1               5                   10                  15

Tyr
```

<210> SEQ ID NO 21
<211> LENGTH: 83
<212> TYPE: DNA
<213> ORGANISM: Artificial Sequence
<220> FEATURE:
<223> OTHER INFORMATION: Synthetic

<400> SEQUENCE: 21

```
gctaacagcg gtgttacttc tgctcctgat actagacctg ctcctggttc tactgcttcc     60
ataaacatag ctagtgtggg tac                                             83
```

<210> SEQ ID NO 22
<211> LENGTH: 83
<212> TYPE: DNA
<213> ORGANISM: Artificial Sequence
<220> FEATURE:
<223> OTHER INFORMATION: Synthetic

<400> SEQUENCE: 22

```
gctaacagct ccggtgttac ttctgctcct gatactagac ctgctcctgg ttctactgct     60
ataaacatag ctagtgtggg tac                                             83
```

<210> SEQ ID NO 23
<211> LENGTH: 83
<212> TYPE: DNA
<213> ORGANISM: Artificial Sequence
<220> FEATURE:
<223> OTHER INFORMATION: Synthetic

<400> SEQUENCE: 23

```
gctaacagct ccataggtgt tacttctgct cctgatacta gacctgctcc tggttctact     60
gctaacatag ctagtgtggg tac                                             83
```

<210> SEQ ID NO 24
<211> LENGTH: 83
<212> TYPE: DNA
<213> ORGANISM: Artificial Sequence
<220> FEATURE:
<223> OTHER INFORMATION: Synthetic

<400> SEQUENCE: 24
gctaacagct ccataaacgg tgttacttct gctcctgata ctagacctgc tcctggttct    60
actgctatag ctagtgtggg tac                                            83

<210> SEQ ID NO 25
<211> LENGTH: 83
<212> TYPE: DNA
<213> ORGANISM: Artificial Sequence
<220> FEATURE:
<223> OTHER INFORMATION: Synthetic

<400> SEQUENCE: 25
gctaacagct ccataaacat aggtgttact tctgctcctg atactagacc tgctcctggt    60
tctactgctg ctagtgtggg tac                                            83

<210> SEQ ID NO 26
<211> LENGTH: 83
<212> TYPE: DNA
<213> ORGANISM: Artificial Sequence
<220> FEATURE:
<223> OTHER INFORMATION: Synthetic

<400> SEQUENCE: 26
gctaacagct ccataaacat agctggtgtt acttctgctc ctgatactag acctgctcct    60
ggttctactg ctagtgtggg tac                                            83

<210> SEQ ID NO 27
<211> LENGTH: 324
<212> TYPE: PRT
<213> ORGANISM: Tomato bushy stunt virus

<400> SEQUENCE: 27

Lys Lys Gln Gln Met Ile Asn His Val Gly Gly Thr Gly Gly Ala Ile
1               5                   10                  15

Met Ala Pro Val Ala Val Thr Arg Gln Leu Val Gly Ser Lys Pro Lys
            20                  25                  30

Phe Thr Gly Arg Thr Ser Gly Ser Val Thr Val Thr His Arg Glu Tyr
        35                  40                  45

Leu Ser Gln Val Asn Asn Ser Thr Gly Phe Gln Val Asn Gly Gly Ile
    50                  55                  60

Val Gly Asn Leu Leu Gln Leu Asn Pro Leu Asn Gly Thr Leu Phe Ser
65                  70                  75                  80

Trp Leu Pro Ala Ile Ala Ser Asn Phe Asp Gln Tyr Thr Phe Asn Ser
                85                  90                  95

Val Val Leu His Tyr Val Pro Leu Cys Ser Thr Thr Glu Val Gly Arg
            100                 105                 110

Val Ala Ile Tyr Phe Asp Lys Asp Ser Glu Asp Pro Glu Pro Ala Asp
        115                 120                 125

Arg Val Glu Leu Ala Asn Tyr Ser Val Leu Lys Glu Thr Ala Pro Trp
    130                 135                 140

Ala Glu Ala Met Leu Arg Val Pro Thr Asp Lys Ile Lys Arg Phe Cys
145                 150                 155                 160

-continued

```
Asp Asp Ser Ser Thr Ser Asp His Lys Leu Ile Asp Leu Gly Gln Leu
            165                 170                 175

Gly Ile Ala Thr Tyr Gly Gly Ala Gly Thr Asn Ala Val Gly Asp Ile
        180                 185                 190

Phe Ile Ser Tyr Ser Val Thr Leu Tyr Phe Pro Gln Pro Thr Asn Thr
    195                 200                 205

Leu Leu Ser Thr Arg Arg Leu Asp Leu Ala Gly Ala Leu Val Thr Ala
210                 215                 220

Ser Gly Pro Gly Tyr Leu Leu Val Ser Arg Thr Ala Thr Val Leu Thr
225                 230                 235                 240

Met Thr Phe Arg Ala Thr Gly Thr Phe Val Ile Ser Gly Thr Tyr Arg
                245                 250                 255

Cys Leu Thr Ala Thr Thr Leu Gly Leu Ala Gly Gly Val Asn Val Asn
            260                 265                 270

Ser Ile Thr Val Val Asp Asn Ile Gly Thr Asp Ser Ala Phe Phe Ile
        275                 280                 285

Asn Cys Thr Val Ser Asn Leu Pro Ser Val Val Thr Phe Thr Ser Thr
    290                 295                 300

Gly Ile Thr Ser Ala Thr Val His Cys Val Arg Ala Thr Arg Gln Asn
305                 310                 315                 320

Asp Val Ser Leu
```

<210> SEQ ID NO 28
<211> LENGTH: 331
<212> TYPE: PRT
<213> ORGANISM: Red clover necrotic mosaic virus

<400> SEQUENCE: 28

```
Lys Ser Lys Gln Arg Ser Gln Pro Arg Asn Arg Thr Pro Asn Thr Ser
1               5                   10                  15

Val Lys Thr Val Ala Ile Pro Phe Ala Lys Thr Gln Ile Ile Lys Thr
            20                  25                  30

Val Asn Pro Pro Lys Pro Ala Arg Gly Ile Leu His Thr Gln Leu
        35                  40                  45

Val Met Ser Val Val Gly Ser Val Gln Met Arg Thr Asn Asn Gly Lys
    50                  55                  60

Ser Asn Gln Arg Phe Arg Leu Asn Pro Ser Asn Pro Ala Leu Phe Pro
65                  70                  75                  80

Thr Leu Ala Tyr Glu Ala Ala Asn Tyr Asp Met Tyr Arg Leu Lys Lys
                85                  90                  95

Leu Thr Leu Arg Tyr Val Pro Leu Val Thr Val Gln Asn Ser Gly Arg
            100                 105                 110

Val Ala Met Ile Trp Asp Pro Asp Ser Gln Asp Ser Ala Pro Gln Ser
        115                 120                 125

Arg Gln Glu Ile Ser Ala Tyr Ser Arg Ser Val Ser Thr Ala Val Tyr
    130                 135                 140

Glu Lys Cys Ser Leu Thr Ile Pro Ala Asp Asn Gln Trp Arg Phe Val
145                 150                 155                 160

Ala Asp Asn Thr Thr Val Asp Arg Lys Leu Val Asp Phe Gly Gln Leu
                165                 170                 175

Leu Phe Val Thr His Ser Gly Ser Asp Gly Ile Glu Thr Gly Asp Ile
            180                 185                 190

Phe Leu Asp Cys Glu Val Glu Phe Lys Gly Pro Gln Pro Thr Ala Ser
        195                 200                 205
```

```
Ile Val Gln Lys Thr Val Ile Asp Leu Gly Gly Thr Leu Thr Ser Phe
    210                 215                 220
Glu Gly Pro Ser Tyr Leu Met Pro Pro Asp Ala Phe Ile Thr Ser Ser
225                 230                 235                 240
Ser Phe Gly Leu Phe Val Asp Val Ala Gly Thr Tyr Leu Leu Thr Leu
                245                 250                 255
Val Val Thr Cys Ser Thr Thr Gly Ser Val Thr Val Gly Gly Asn Ser
                260                 265                 270
Thr Leu Val Gly Asp Gly Arg Ala Ala Tyr Gly Ser Ser Asn Tyr Ile
            275                 280                 285
Ala Ser Ile Val Phe Thr Ser Ser Gly Val Leu Ser Thr Thr Pro Ser
    290                 295                 300
Val Gln Phe Ser Gly Ser Ser Gly Val Ser Arg Val Gln Met Asn Ile
305                 310                 315                 320
Cys Arg Cys Lys Gln Gly Asn Thr Phe Ile Leu
                325                 330
```

<210> SEQ ID NO 29
<211> LENGTH: 41
<212> TYPE: PRT
<213> ORGANISM: Red clover necrotic mosaic virus

<400> SEQUENCE: 29

```
Ala Ser Ile Val Gln Lys Thr Val Ile Asp Leu Gly Gly Thr Leu Thr
1               5                   10                  15
Ser Phe Glu Gly Pro Ser Tyr Leu Met Pro Pro Asp Ala Phe Ile Thr
            20                  25                  30
Ser Ser Ser Phe Gly Leu Phe Val Asp
        35                  40
```

<210> SEQ ID NO 30
<211> LENGTH: 27
<212> TYPE: PRT
<213> ORGANISM: Red clover necrotic mosaic virus

<400> SEQUENCE: 30

```
Ala Ser Ile Val Gln Lys Tyr Val Ile Asp Leu Gly Gly Thr Leu Thr
1               5                   10                  15
Ser Phe Glu Gly Pro Ser Tyr Leu Met Pro Pro
            20                  25
```

<210> SEQ ID NO 31
<211> LENGTH: 51
<212> TYPE: DNA
<213> ORGANISM: Red clover necrotic mosaic virus

<400> SEQUENCE: 31
agcatcgtac agaaaactgt aattgatctc ggtgggacac tcacttcttt c         51

<210> SEQ ID NO 32
<211> LENGTH: 17
<212> TYPE: PRT
<213> ORGANISM: Red clover necrotic mosaic virus

<400> SEQUENCE: 32

```
Ser Ile Val Gln Lys Thr Val Ile Asp Leu Gly Gly Thr Leu Thr Ser
1               5                   10                  15
Phe
```

<210> SEQ ID NO 33
<211> LENGTH: 78
<212> TYPE: DNA
<213> ORGANISM: Artificial Sequence
<220> FEATURE:
<223> OTHER INFORMATION: Synthetic

<400> SEQUENCE: 33
gaaaactgta ggtgttactt ctgctcctga tactagacct gctcctggtt ctactgctat    60
tgatctcggt gggacgtt    78

<210> SEQ ID NO 34
<211> LENGTH: 78
<212> TYPE: DNA
<213> ORGANISM: Artificial Sequence
<220> FEATURE:
<223> OTHER INFORMATION: Synthetic

<400> SEQUENCE: 34
gaaaactgta attggtgtta cttctgctcc tgatactaga cctgctcctg gttctactgc    60
tgatctcggt gggacgtt    78

<210> SEQ ID NO 35
<211> LENGTH: 78
<212> TYPE: DNA
<213> ORGANISM: Artificial Sequence
<220> FEATURE:
<223> OTHER INFORMATION: Synthetic

<400> SEQUENCE: 35
gaaaactgta attgatggtg ttacttctgc tcctgatact agacctgctc ctggttctac    60
tgctctcggt gggacgtt    78

<210> SEQ ID NO 36
<211> LENGTH: 78
<212> TYPE: DNA
<213> ORGANISM: Artificial Sequence
<220> FEATURE:
<223> OTHER INFORMATION: Synthetic

<400> SEQUENCE: 36
gaaaactgta attgatctcg gtgttacttc tgctcctgat actagacctg ctcctggttc    60
tactgctggt gggacgtt    78

<210> SEQ ID NO 37
<211> LENGTH: 78
<212> TYPE: DNA
<213> ORGANISM: Artificial Sequence
<220> FEATURE:
<223> OTHER INFORMATION: Synthetic

<400> SEQUENCE: 37
gaaaactgta attgatctcg gtggtgttac ttctgctcct gatactagac ctgctcctgg    60
ttctactgct gggacgtt    78

<210> SEQ ID NO 38
<211> LENGTH: 78
<212> TYPE: DNA
<213> ORGANISM: Artificial Sequence
<220> FEATURE:
<223> OTHER INFORMATION: Synthetic -continued

```
<400> SEQUENCE: 38
gaaaactgta attgatctcg gtgggggtgt tacttctgct cctgatacta gacctgctcc     60
tggttctact gctacgtt                                                   78
```